United States Patent [19]

Humbert et al.

[11] 4,294,845

[45] Oct. 13, 1981

[54] 1,3-BENZODIOXIN DERIVATIVES

[76] Inventors: Daniel Humbert, Fontenay-sous-Bois; Francois Clemence, Paris; Michele Dagnaux, Fontenay-sous-Bois, all of France

[21] Appl. No.: 34,431

[22] Filed: Apr. 30, 1979

Related U.S. Application Data

[63] Continuation-in-part of Ser. No. 847,776, Nov. 2, 1977, abandoned.

[30] Foreign Application Priority Data

May 3, 1978 [FR] France ................... 78 13094

[51] Int. Cl.³ .............. A61K 31/335; C07D 319/08
[52] U.S. Cl. ...................... 424/278 Q; 260/340.3; 260/340.9 R; 568/722
[58] Field of Search ............ 260/340.9 R, 340.3; 424/278

[56] References Cited

U.S. PATENT DOCUMENTS

| | | | |
|---|---|---|---|
| 3,835,159 | 9/1974 | Najer et al. | 260/340.3 |
| 3,836,543 | 9/1974 | Grisar | 260/340.3 |
| 4,046,762 | 9/1977 | Manghisi et al. | 260/340.3 X |
| 4,056,540 | 11/1977 | Buchanan et al. | 260/340.3 |

FOREIGN PATENT DOCUMENTS 1312893  11/1962  France ................ 260/340.3

*Primary Examiner*—Ethel G. Love

*Attorney, Agent, or Firm*—Hammond & Littell, Weissenberger and Muserlian

[57] ABSTRACT

Novel racemic mixtures or optically active isomers of 1,3-benzodioxins of the formula

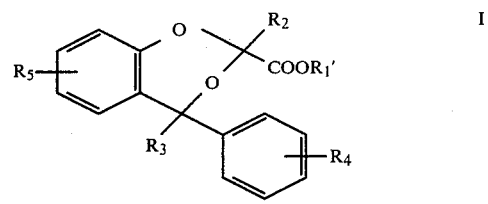

wherein $R_1'$ is selected from the group consisting of hydrogen, alkali metal, alkaline earth metal, —NH₄, aluminum, non-toxic, pharmaceutically acceptable amines, alkyl of 1 to 5 carbon atoms, 2,3-dihydroxypropanyl, (2,2-dimethyl-1,3-dioxolan-4-yl)methyl and dialkylaminoalkyl with alkyls of 1 to 4 carbon atoms, $R_2$ is selected from the group consisting of hydrogen and alkyl of 1 to 5 carbon atoms, $R_3$ is selected from the group consisting of hydrogen, alkyl of 1 to 5 carbon atoms and phenyl and $R_4$ and $R_5$ are individually selected from the group consisting of hydrogen and halogen, and the non-toxic, pharmaceutically acceptable acid addition salts where $R_1'$ is dialkylaminoalkyl, with the proviso that $R_2$ and $R_3$ are not hydrogen simultaneously having hypolipemic activity and their preparation.

30 Claims, No Drawings

1,3-BENZODIOXIN DERIVATIVES

PRIOR APPLICATION

This application is a continuation in part of a copending application Ser. No. 847,776 filed Nov. 2, 1977, now abandoned.

STATE OF THE ART

U.S. Pat. No. 4,056,540 describes 2-aminoalkyl or 2-amino-4-phenyl-1,3-benzodioxan compounds which are stated as having anticonvulsant or antiarrhythmia activity.

OBJECTS OF THE INVENTION

It is an object of the invention to provide the novel 1,3-benzodioxins of formula I and their non-toxic, pharmaceutically acceptable acid addition salts where appropriate and a novel process for their preparation and novel intermediates.

It is another object of the invention to provide novel hypolipemic activity in warm-blooded animals.

These and other objects and advantages of the invention will become obvious from the following detailed description.

THE INVENTION

The novel products of the invention are selected from the group consisting of racemic mixtures or optically active isomers of 1,3-benzodioxins of the formula

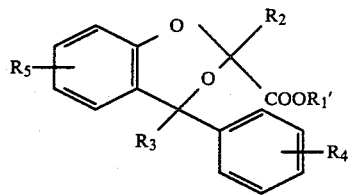

wherein $R_1'$ is selected from the group consisting of hydrogen, alkali metal, alkaline earth metal, —$NH_4$, aluminum, non-toxic, pharmaceutically acceptable amines, alkyl of 1 to 5 carbon atoms, 2,3-dihydroxypropanyl, (2,2-dimethyl-1,3-dioxolan-4-yl)-methyl and dialkylaminoalkyl with alkyls of 1 to 4 carbon atoms, $R_2$ is selected from the group consisting of hydrogen and alkyl of 1 to 5 carbon atoms, $R_3$ is selected from the group consisting of hydrogen, alkyl of 1 to 5 carbon atoms and phenyl, and $R_4$ and $R_5$ are individually selected from the group consisting of hydrogen and halogen, and the non-toxic, pharmaceutically acceptable acid addition salts where $R_1'$ is dialkylaminoalkyl with the proviso that $R_2$ and $R_3$ are not hydrogen simultaneously.

A preferred group of compounds of formula I are those wherein $R_1'$ is selected from the group consisting of hydrogen, alkyl of 1 to 5 carbon atoms, alkali metal, alkaline earth metal, aluminum, —$NH_4$ and amines and $R_2$, $R_3$, $R_4$ and $R_5$ have the above definitions.

Examples of alkyls of 1 to 5 carbon atoms are methyl, ethyl, n-propyl, isopropyl, n-butyl, isobutyl, tert.-butyl and pentyl. Examples of halogens are chlorine, bromine and fluorine. Examples of alkali metal and alkaline earth metals are sodium, potassium, lithium and calcium. Examples of suitable amines are monoalkylamines such as methylamine, ethylamine and propylamine; dialkylamines such as dimethylamine, diethylamine and di-n-propylamine; and trialkylamines such as triethylamine; as well as piperidine, morpholine, piperazine or pyrrolidine. Examples of dialkylaminoalkyl with alkyls of 1 to 4 carbon atoms is dimethylaminoethyl.

Examples of suitable acids for the non-toxic, pharmaceutically acceptable acid addition salts are inorganic acids such as hydrochloric acid, hydrobromic acid, hydroiodic acid, nitric acid, sulfuric acid and phosphoric acid and organic acids such as acetic acid, maleic acid, fumaric acid, succinic acid, tartaric acid, alkylsulfonic acids such as methansulfonic acid, ethanesulfonic acid, propanesulfonic acid, alkyldisulfonic acids such as $\alpha,\beta$-ethane-disulfonic acid.

The expression "mixture of isomers" is intended to include racemic mixtures of isomers or mixtures of optically active isomers in any proportions. It is particularly intended to include mixtures of racemates in any proportion, mixtures of 2 optical antipodes in any proportion and mixtures of two optically active diastereoisomers in any proportions.

Among the preferred compounds of the invention of formula I are those wherein $R_1'$ is selected from the group consisting of hydrogen, alkali metal, alkaline earth metal, —$NH_4$, aluminum, amines and methyl, $R_2$ is methyl or hydrogen, $R_3$ is hydrogen, methyl or phenyl, $R_4$ is hydrogen and $R_5$ is hydrogen or chlorine in racemic form, or optically active form or in the form of mixtures of isomers or those wherein $R_1'$ is hydrogen, alkali metal, alkaline earth metal, —$NH_4$, aluminum, amines or methyl, $R_2$ and $R_4$ are hydrogen, $R_3$ is hydrogen, methyl or phenyl and $R_5$ is chlorine in racemic form, or optically active form or in the form of mixtures of isomers.

Examples of specific preferred compounds of the invention are methyl 6-chloro-4-methyl-4-phenyl-[4H]-1,3-benzodioxin-2-carboxylate, methyl 6-chloro-4-methyl-4-(3-chlorophenyl)-[4H]-1,3-benzodioxin-2-carboxylate, ethyl 6-chloro-4-methyl-4-phenyl-[4H]-1,3-benzodioxin-2-carboxylate, 6-chloro-4-methyl-4-phenyl-[4H]-1,3-benzodioxin-2-carboxylic acid and its sodium salt, 6-chloro-2,4-dimethyl-4-phenyl-[4H]-1,3-benzodioxin-2-carboxylic acid, 6-chloro-4-methyl-4-(3-chlorophenyl)-[4H]-1,3-benzodioxin-2-carboxylic acid, the d and l isomers of 6-chloro-4-methyl-4-phenyl-[4H]-1,3-benzodioxin-2-carboxylic acid, piperidine salts of 2 racemate A and B diastereoisomers of 6-chloro-4-methyl-4-phenyl-[4H]-1,3-benzodioxin-2-carboxylic acid, d and l isomers of two racemate A and B diastereoisomers of 6-chloro-4-methyl-4-phenyl-[4H]-1,3-benzodioxin-2-carboxylic acid and racemic and optically active forms of (2,2-dimethyl-1,3-dioxolan-4-yl)-methyl 6-chloro-4-methyl-4-phenyl-[4H]-1,3-benzodioxin-2-carboxylate, 2,3-dihydroxypropanyl 6-chloro-4-methyl-4-phenyl-[4H]-1,3-benzodioxin-2-carboxylate and methyl 7-chloro-4-methyl-4-phenyl-[4H]-1,3-benzodioxin-2-carboxylate and 2-(diethylamino)-ethyl 6-chloro-4-methyl-4-phenyl-[4H]-1,3-benzodioxin-2-carboxylate and the non-toxic and 2-(dimethylamino)-ethyl-6-chloro-4-methyl-4-phenyl-|4H|-1,3-benzodioxin-2-carboxylate, pharmaceutically acceptable acid addition salts of these two latter.

Among the preferred compounds of the invention of formula I, there is also to be mentioned the A isomer of the 7-chloro-4-methyl-4-phenyl-[4H]-1,3-benzodioxin-2-carboxylic acid having a RMN Spectrum (deuterochloroform, basic frequency 60 MHz): 2 hydrogen at 312 Hz and 4-$CH_3$ at 116 Hz, 2-(dimethylamino)-ethyl 6-chloro-4-methyl-4-phenyl-[4H]-1,3-benzodioxin-2-carboxylate, mixtures or optically active isomers and acid addition salts thereof and preferably the hydrochloride of A-isomer of 2-(dimethylamino)-ethyl 6-chloro-4-methyl-4-phenyl-[4H]-1,3-benzodioxin-2-carboxylate having a RMN Spectrum (deuterochloroform, basic frequency 60 MHz) 2-hydrogen at 312 Hz and 4-$CH_3$ at 115 Hz.

The term-isomer A-designates one or the other of two racemic diastereoisomer forms of the products of formula I which possesses two asymetrical carbon atoms.

The novel process of the invention for the preparation of a compound of formula I wherein $R_1'$ is hydrogen comprises reacting in the presence of a basic condensation agent a compound of the formula

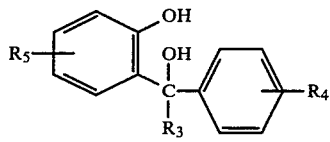

wherein $R_3$, $R_4$ and $R_5$ have the above definition with an alkali metal salt of an acid of the formula

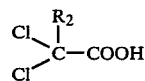

wherein $R_2$ has the above definition to obtain the alkali metal salt of the compound of formula I, optionally treating the latter with an acid to form the corresponding free acid of formula I which may be salified or esterified to obtain the corresponding salts or esters of formula I. In each case, the compounds of formula I may be recovered in the form of racemic mixtures, optically active isomers or mixtures of the isomers.

In the said process, the alkali metal salt of the compound of formula III is preferably sodium, potassium or lithium and the basic condensation agent is alkali metal alkylate such as sodium methylate, sodium ethylate or sodium tert.-butylate; an alkali metal hydride such as sodium hydride or potassium hydride; or an alkali metal amide such as sodium amide, potassium amide or lithium amide, or sodium. The reaction is preferably effected in an organic solvent such as benzene, toluene, xylene, ethyl ether, dioxane, dimethylformamide, tetrahydrofuran, hexamethylphosphorotriamide or mixtures thereof.

The process can also be operated in the presence of a compound which serves as a catalyst of the ether-couronne type such as dibenzo-18-couronne-6, dicyclohexyl-18-couronne-6 or 18-couronne-6, preferably in a mixture with an organic solvent such as dioxane.

The reaction is effected at a temperature from −10° C. to the reflux temperature of the reaction mixture. Preferably, the compound of formula II is reacted with the basic condensation agent before the reaction with the salt of the compound of formula III.

The compounds of formula I wherein $R_1'$ is alkyl of 1 to 5 carbon atoms may be prepared by esterification of the corresponding acid with an alcohol of the formula R′—OH wherein R′ is alkyl of 1 to 5 carbon atoms, preferably in the presence of an acid such as hydrochloric acid, p-toluene sulfonic acid or in the presence of a acid resin.

The said esters of formula I may also be prepared by trans esterification. When $R_1'$ is methyl, the compounds of formula I may be prepared by reacting the compounds of formula I wherein $R_1'$ is hydrogen with diazomethane in an organic solvent. The esters may also be prepared by using a functional derivative of the acid of formula I such as its acid chloride which can be prepared in a known manner.

The various salts of the compounds of formula I may be prepared by reacting the free acid with the corresponding basis. The base may be an inorganic or organic base such as sodium hydroxide, potassium hydroxide, lithium hydroxide, calcium hydroxide, aluminum hydroxide, sodium ethylate, potassium ethylate, ammonium hydroxide or amines such as methylamine, ethylamine, propylamine, dimethylamine, diethylamine, dipropylamine, triethylamine, piperidine, morpholine, piperazine or pyrrolidine. The reaction is preferably effected in one or more solvents such as water, ethyl ether, ethanol, acetone or ethyl acetate.

The process of the invention for preparation of the compounds of formula I wherein $R_1'$ is 2,3-dihydroxypropanyl, dialkylaminoalkyl or (2,2-dimethyl-1,3-dioxolan-4-yl)-methyl comprises treating the corresponding acid of formula I wherein $R_1'$ is hydrogen or a functional derivative thereof with an alcohol of the formula R′-OH wherein R′ is dialkylaminoalkyl with alkyls of 1 to 4 carbon atoms or (2,2-dimethyl-1,3-dioxolan-4-yl)-methyl to form the corresponding ester and when R′ is dialkylaminoalkyl, optionally treating the same with an acid to form the corresponding acid addition salt and when R′ is (2,2-dimethyl-1,3-dioxolan-4-yl)-methyl, optionally treating the ester with a hydrolysis agent to form the compound of formula I wherein $R_1'$ is 2,3-dihydroxypropanyl. The products may be in the form of racemic mixtures, optically active isomers or mixtures of the isomers.

Preferably, the acid derivative is an ester or acid halide and the same is prepared from the acid by known methods and the reaction is effected in an organic solvent such as benzene, toluene, xylene or ethyl ether. The salification is effected in the usual manner and the hydrolysis is preferably effected with an acid such as hydrochloric acid.

The compounds of formula I wherein $R_4$ and $R_5$ are hydrogen may be prepared by reacting a compound of formula I wherein at least one of $R_4$ and $R_5$ is chlorine with hydrogen in the presence of a catalyst, preferably palladium. Preferably, the reaction is effected in an alkaline medium with a base such as triethylamine, trimethylamine, dimethylaniline or pyridine and in an organic solvent such as methanol, ethanol or isopropanol.

The compounds of formula I for certain values of $R_3$ and $R_4$ have an asymetric carbon in both the 2- and 4-positions. The compounds of formula II for certain values of $R_3$ and $R_4$ have an asymetric carbon. The reaction of the compounds of formulae II and III leads to a product of formula I containing a sole asymetric carbon atom in the form of a racemic mixture which can be resolved into its optical antipodes by known methods such as the formation of salts with optically active bases. The product of formula II may be used either as a racemic mixture or in the optically active form.

The racemates or the optically active diastereoisomers of formula I (which are designated as cis and trans)

can be separated by known methods such as selective crystallization, by counter-current extraction or by column chromatography. The racemates may be resolved into their optical enantiomers by known methods such as formation of salts with optically active bases. The different isomeric forms can equally be mixed in order to obtain the desired mixture.

The novel hypolipemiant compositions of the invention are comprised of a hypolipemiantly effective amount of at least one compound selected from the group consisting of racemic mixtures or optically active isomers of 1,3-benzodioxins of the formula

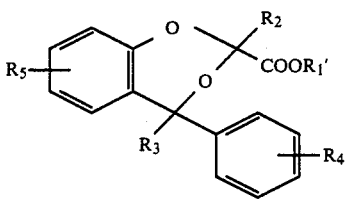

wherein $R_1'$ is selected from the group consisting of hydrogen, alkali metal, alkaline earth metal, $-NH_4$, aluminum, non-toxic, pharmaceutically acceptable amines, alkyl of 1 to 5 carbon atoms, 2,3-dihydroxy-propanyl, (2,2-dimethyl-1,3-dioxolan-4-yl)-methyl and dialkylaminoalkyl with alkyls of 1 to 4 carbon atoms, $R_2$ is selected from the group consisting of hydrogen and alkyl of 1 to 5 carbon atoms, $R_3$ is selected from the group consisting of hydrogen, alkyl of 1 to 5 carbon atoms and phenyl and $R_4$ and $R_5$ are individually selected from the group consisting of hydrogen and halogen and the non-toxic, pharmaceutically acceptable acid addition salts where $R_1'$ is dialkylaminoalkyl and an inert pharmaceutical carrier or excipient. The composition may be in the form of tablets, dragees, gelules, granules, suppositories or injectable solutions or suspensions formed in the usual manner.

Examples of suitable excipients are talc, arabic gum, lactose, starch, magnesium stearate, cacao butter, aqueous or non-aqueous vehicles, fatty bodies of animal or vegetable origin, paraffinic derivatives, glycols, diverse wetting agents, dispersants or emulsifiers and preservatives.

Among the preferred compounds of formula I are those wherein $R_1'$ is hydrogen, alkali metal, alkaline earth metal, aluminum, ammonium or an amine or methyl, $R_2$ is hydrogen or methyl, $R_3$ is hydrogen, methyl or phenyl, $R_4$ is hydrogen and $R_5$ is hydrogen or chlorine and those wherein $R_1'$ is hydrogen, alkali metal, alkaline earth metal, aluminum, ammonium or an amine or methyl, $R_2$ and $R_4$ are hydrogen, $R_3$ is hydrogen, methyl or phenyl and $R_5$ is chlorine.

The compositions due to their remarkable hypolipemiant activity reduce the plasmatic levels of lipids, triglycerides and cholestrol and are useful for the treatment of acute or chronic hyperlipemaia, cardiac insufficiencies of atheromatous origin and chronic angina states.

The novel method of the invention for inducing hypolipemiant activity in warm-blooded animals, including humans, comprises administering to warm-blooded animals a hypolipemiantly effective amount of at least one compound selected from the group consisting of racemic mixtures or optically active isomers of 1,3-benzodioxins of the formula

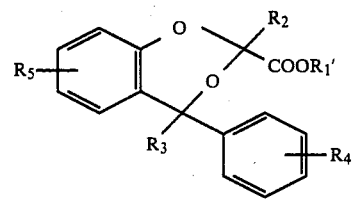

wherein $R_1'$ is selected from the group consisting of hydrogen, alkali metal, alkaline earth metal, $-NH_4$, aluminum, non-toxic, pharmaceutically acceptable amines, alkyl of 1 to 5 carbon atoms, 2,3-dihydroxy-propanyl, (2,2-dimethyl-1,3-dioxolan-4-yl)-methyl and dialkylaminoalkyl with alkyls of 1 to 4 carbon atoms, $R_2$ is selected from the group consisting of hydrogen and alkyl of 1 to 5 carbon atoms, $R_3$ is selected from the group consisting of hydrogen, alkyl of 1 to 5 carbon atoms and phenyl and $R_4$ and $R_5$ are individually selected from the group consisting of hydrogen and halogen and the non-toxic, pharmaceutically acceptable acid addition salts where $R_1'$ is dialkylaminoalkyl. The compounds may be administered orally, rectally or parenterally and the usual dose is 1 to 20 mg/kg depending on the compound by oral route.

The novel intermediates of the invention are in the form of racemic mixtures or optically active isomers of 5-chloro-2-hydroxy-α-methyl-α-phenyl-benzene-methanol and of 4-chloro-2-hydroxy-α-methyl-α-phenyl-benzene-methanol and compounds of the formula

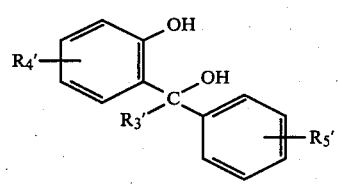

wherein $R_4'$ is chlorine or fluorine, $R_5'$ is chlorine, $R_3'$ is alkyl of 2 to 4 carbon atoms and when $R_4'$ is fluorine, $R_3'$ may be methyl.

The compounds of formula II which are not known where $R_3$ is hydrogen may be prepared by reducing a compound of the formula

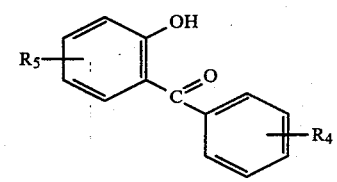

with a reducing agent such as a mixed hydride in an organic solvent. The compounds of formula II wherein $R_3$ is alkyl of 1 to 5 carbon atoms or phenyl may be prepared by reacting a compound of formula A in an organic solvent with an organo magnesium halide of the formula

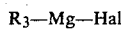

wherein $R_3$ is alkyl of 1 to 5 carbon atoms or phenyl and Hal is chlorine or bromine.

The compounds of formula II may also be prepared by reacting in an organic solvent a compound of formula

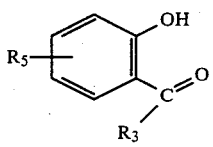 (B)

wherein $R_3$ and $R_5$ have the above definition with an organo magnesium halide of the formula

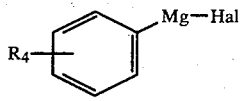

wherein $R_4$ has the above definition and Hal is an halogen such as chlorine or bromine.

In the following examples there are described several preferred embodiments to illustrate the invention. However, it is to be understood that the invention is not intended to be limited to the specific embodiments.

EXAMPLE 1

6-chloro-4-methyl-4-phenyl-[4H]-1,3-benzodioxin-2-carboxylic acid (mixture of two racemates diastereoisomers)

STEP A: 5-chloro-2-hydroxy-α-methyl-α-phenyl-benzenemethanol 14 g of magnesium turnings were dispensed with stirring in 100 ml of anhydrous ether and a solution of 76 g of methyl iodide in 200 ml of anhydrous ether was added dropwise thereto. The mixture was refluxed for one hour and was then cooled to 15°–20° C. and a solution of 59 g of 5-chloro-2-hydroxybenzophenone in 250 ml of anhydrous benzene was added at the said temperature. Part of the ether was distilled and the mixture was then refluxed for 2 hours. The mixture was cooled to 5°–10° C. and 250 ml of 3 N hydrochloric acid were added thereto dropwise. The organic phase was decanted and the aqueous phase was washed twice with 100 ml of benzene. The benzene extracts were washed with water, then with saturated sodium bicarbonate solution and then twice with 50 ml of water, were dried over magnesium sulfate and evaporated to dryness under reduced pressure to obtain 58.9 g of crystals. The crystals were crystallized from petroleum ether (b.p.=60°–80° C.) to obtain 53 g of 5-chloro-2-hydroxy-α-methyl-α-phenylbenzene methanol melting at 106° C.

Analysis: $C_{14}H_{13}ClO_2$: Calculated: %C 67.61; %H 5.27; %Cl 14.26. Found: %C 67.8; %H 5.4; %Cl 14.2.

STEP B: 6-chloro-4-methyl-4-phenyl-[4H]-1,3-benzodioxin-2-carboxylic acid

A solution of 24.9 g of the product of Step A in 250 ml of toluene was added dropwise with stirring at a mixture of 8.1 g of sodium amide in 100 ml of toluene and the mixture was refluxed for 4½ hours and was cooled to room temperature. 18 g of potassium dichloroacetate were added in small fractions with stirring and after the addition of 20 ml of hexamethylphosphortriamide thereto, the mixture was refluxed for 5 hours and then was cooled to room temperature. 10 ml of ethyl acetate were slowly added thereto and then 250 ml of water were added dropwise. The aqueous phase was recovered and the organic phase was extracted 3 times with 100 ml of water. The combined aqueous phase containing the potassium salt of the desired acid were washed three times with 100 ml of ether and was acidified by bubbling sulfur dioxide therethrough. The mixture was extracted 4 times with 100 ml of ether and the ether extracts were washed 3 times with 50 ml of water, were dried over magnesium sulfate, treated with activated carbon and evaporated to dryness under reduced pressure to obtain 24 g of raw product. The latter was crystallized from 100 ml of a 9-1 cyclohexane-benzene mixture and the crystals were dried to obtain 15.2 g of racemic 6-chloro-4-phenyl-4-methyl-[4H]-1,3-benzodioxin-2-carboxylic acid melting at 142° C.

Analysis: $C_{16}H_3ClO_4$ Calculated: %C 63.06; %H 4.30; %Cl 11.63. Found: %C 63.3; %H 4.4; %Cl 11.5.

EXAMPLE 2

A and B isomers of methyl 6-chloro-4-methyl-4-phenyl-[4H]-1,3-benzodioxin-2-carboxylate A solution of 3.3 g of the Product of Example 1 in 75 ml of methylene chloride was added dropwise at 5° C. to a solution of 2.25 g of diazomethane in 150 ml of methylene chloride and the mixture was stirred for one hour and then allowed to stand for 24 hours at room temperature. 10 ml of acetic acid were added and the mixture was evaporated to dryness under reduced pressure to obtain 4.2 g of a mixture of two diastereoisomer racemates. The said product was chromatographed over silica gel and was eluted with a 2-8 ethyl ether-petroleum ether (b.p.=60°–80° C.) mixture to obtain 1 g of the A isomer of methyl 6-chloro-4-methyl-4-phenyl-[4H]-1,3-benzodioxin-2-carboxylate melting at 114°–115° C.

Analysis: $C_{17}H_{15}ClO_4$: Calculated: %C 64.06; %H 4.74; %Cl 11.12. Found: %C 63.9; %H 4.7; %Cl 11.4.

RMN Spectrum (60 Hz):

$CH_3$ at 117 Hz; $COOCH_3$ at 232 Hz; 2-hydrogen at 311 Hz; aromatic ring at 410 to 445 Hz.

Also obtained were 0.6 g of the B isomer of 6-chloro-4-methyl-4-phenyl-[4H]-1,3-benzodioxin-2-carboxylate melting at 102° C.

Analysis: $C_{17}H_{15}ClO_4$: Calculated: %C 64.06; %H 4.74; %Cl 11.12. Found: %C 64.0; %H 4.8; %Cl 11.3.

RMN Spectrum (60 Hz):

$CH_3$ at 125 Hz; $COOCH_3$ at 228 Hz; 2-hydrogen at 341 Hz; aromatic ring at 405 to 445 Hz.

EXAMPLE 3

A isomer of 6-chloro-4-methyl-4-phenyl-[4H]-1,3-benzodioxin-2-carboxylic acid

A mixture of 14 g of the A isomer of Example 2, 2.8 g of potassium hydroxide pastilles, 32 ml of water and 160 ml of methanol were stirred for 22 hours at room temperature and then 320 ml of water were added thereto. The aqueous phase was washed twice with 160 ml of ether and was acidified with 2 N hydrochloric acid. The precipitate was extracted 3 times with 320 ml of ether and the ether extracts were washed twice with 160 ml of water, dried over magnesium sulfate and evaporated to dryness to obtain 13 g of crystals 3.9 g of which were crystallized from 100 ml of a 2-8 ethyl acetate-cyclohexane mixture to obtain 3.3 g of the A isomer of 6-chloro-4-methyl-4-phenyl-[4H]-1,3-benzodioxin-2-carboxylic acid melting at 175°–176° C.

Analysis: $C_{15}H_{13}ClO_4$: Calculated: %C 63.06; %H 4.30; %Cl 11.63. Found: %C 63.3; %H 4.6; %Cl 11.3.
RMN Spectrum (60 Hz):
$CH_3$ at 117 Hz; 2-hydrogen at 313 Hz; COOH at 468 Hz; aromatic ring at 412 to 443 Hz.

EXAMPLE 4

B isomer of 6-chloro-4-methyl-4-phenyl-[4H]-1,3-benzodioxin-2-carboxylic acid

A mixture of 5.3 g of the B isomer of Example 2, 10 ml of water, 1.2 g of potassium hydroxide pastilles and 50 ml of methanol was stirred for 20 hours at room temperature and 200 ml of water were added thereto. The aqueous phase was washed twice with 80 ml of ether and was acidified with 2 N hydrochloric acid. The mixture was extracted 3 times with 100 ml of ether and the ether extracts were washed twice with 80 ml of water, dried over magnesium sulfate and evaporated to dryness under reduced pressure to obtain 4.8 g of crystals which were crystallized from an 8-2 cyclohexane-ethyl acetate mixture to obtain after drying 4.4 g of the B isomer of 6-chloro-4-methyl-4-phenyl-[4H]-1,3-benzodioxin-2-carboxylic acid melting at 171° C.

Analysis: $C_{16}H_{13}O_4Cl$: Calculated: %C 63.06; %H 4.30; %Cl 11.63. Found: %C 63.1 %H 4.4; %Cl 11.7.
RMN Spectrum (60 Hz):
$CH_3$ at 124 Hz; COOH at 329 Hz; 2-hydrogen at 341 Hz; aromatic ring at 408–445 Hz.

EXAMPLE 5

6-chloro-2,4-dimethyl--4-phenyl-[4H]-1,3-benzodioxin-2-carboxylic acid (mixture of two racemates diastereoisomers)

A dispersion of 24.9 g of 5-chloro-2-hydroxy-α-methyl-α-phenyl-benzenemethanol in 250 ml of toluene was added dropwise with stirring to a mixture of 8 g of sodium amide in 100 ml of toluene and the mixture was refluxed for 6 hours and was then cooled to room temperature. 17 g of sodium dichloropropionate were added thereto in small portions and the mixture was refluxed for 6 hours and was then cooled to room temperature. 700 ml of water were added thereto and the mixture was acidified with N hydrochloric acid solution. The mixture was made alkaline again with a saturated sodium bicarbonate solution and the aqueous phase was washed 3 times with 100 ml of ether and was acidified with 2 N hydrochloric acid. The aqueous phase was extracted 3 times with 100 ml of ether and the combined organic phases were washed 3 times with 80 ml of water, dried over magnesium sulfate and evaporated to dryness under reduced pressure to obtain 23 g of 6-chloro-2,4-dimethyl-4-phenyl-[4H]-1,3-benzodioxin-2-carboxylic acid (mixture of two racemates diastereoisomers) melting at 181° C.

Analysis: $C_{17}H_{15}ClO_4$: Calculated: %C 64.06; %H 4.74; %Cl 11.12. Found: %C 64.0; %H 4.8; %Cl 11.2.

EXAMPLE 6

A and B isomers of methyl 6-chloro-2,4-dimethyl-4-phenyl-[4H]-1,3-benzodioxin-2-carboxylate A mixture of 23 g of the product of Example of 5 100 g of Redex CF resin (strong sulfonic acid cationic resin) and 250 ml of methanol was refluxed for 20 hours and was cooled to room temperature and was vacuum filtered to remove the resin. The filter was rinsed with methanol and the filtrate was evaporated to dryness under reduced pressure. The 20 g of residue was chromatographed over 1.56 g of silica gel under pressure and was eluted with a 2-8 ethyl ether-petroleum ether (b.p.=60°-80° C.) mixture to obtain 1.7 g of the A isomer of methyl 6-chloro-2,4-dimethyl-4-phenyl-[4H]-1,3-benzodioxin-2-carboxylate melting at 134° C.

Analysis: $C_{18}H_{17}ClO_4$: Calculated: %C 64.96; %H 5.15; %Cl 10.65. Found: %C 65.2; %H 5.2; %Cl 10.9.
RMN Spectrum (60 Hz):
$CH_3$ at 103 and 113 Hz; $COOCH_3$ at 172 Hz; aromatic ring at 419 to 477 Hz.

8.2 g of the B isomer of methyl 6-chloro-2,4-dimethyl-4-phenyl-[4H]-1,3-benzodioxin-2-carboxylate in the form of an oil were also obtained.

Analysis: $C_{18}H_{17}ClO_4$: Calculated: %C 64.96; %H 5.15; %Cl 10.65. Found: %C 65.8; %H 5.1; %Cl 10.8.
RMN Spectrum (60 Hz):
$CH_3$ at 106 and 117 Hz; $COOCH_3$ at 224 Hz; aromatic ring at 415 to 455 Hz.

EXAMPLE 7

A isomer of 6-chloro-2,4-dimethyl-4-phenyl-[4H]-1,3-benzodioxin-2-carboxylic acid A mixture of 1.6 g of the A isomer of Example 6, 20 ml of methanol 2 ml of water and 0.56 g of potassium hydroxide pastilles was stirred for 48 hours at room temperature and 100 ml of water were added thereto. The aqueous phase was washed 3 times with 50 ml of ether and was then acidified with 2 N hydrochloric acid. The aqueous phase was extracted 4 times with 50 ml of ether and the combined ether extracts were washed 3 times with 50 ml of water, dried over magnesium sulfate and evaporated to dryness under reduced pressure to obtain 1.5 g of residue which was crystallized from 80 ml of cyclohexane to obtain 1.2 g of the A isomer of 6-chloro-2,4-dimethyl-4-phenyl-[4H]-1,3-benzodioxin-2-carboxylic acid melting at 184° C.

Analysis: $C_{17}H_{15}O_4Cl$: Calculated: %C 64.06; %H 4.74; %Cl 11.12. Found: %C 64.1; %H 4.8; %Cl 11.1.
RMN Spectrum (60 Hz):
$CH_3$ at 101.5 and 113 Hz; COOH at 342 Hz; aromatic ring at 412 to 442 Hz.

EXAMPLE 8

B isomer of 6-chloro-2,4-dimethyl-4-phenyl-[4H]-1,3-benzodioxin-2-carboxylic acid A mixture of 0.8 g of the B isomer of Example 6, 80 ml of methanol, 8 ml of water and 2.8 g of potassium hydroxide pastilles was stirred at room temperature for 24 hours and 150 ml of water was added thereto. The aqueous phase was washed 3 times with 60 ml of ether and was acidified with 2 N hydrochloric acid solution. The aqueous phase was then extracted 4 times with 60 ml of ethyl ether and the combined ether extracts were washed twice with 80 ml of water, dried over magnesium sulfate and evaporated to dryness under reduced pressure to obtain 7.2 g of residue which was crystallized from 80 ml of cyclohexane and dried to obtain 4.5 g of the B isomer of 6-chloro-2,4-dimethyl-4-phenyl-[4H]-1,3-benzodioxin-2-carboxylic acid melting at 125° C.

Analysis: $C_{17}H_{15}ClO_4$: Calculated: %C 64.06; %H 4.74; %Cl 11.12. Found: %C 64.2; %H 5.0; %Cl 11.2.
RMN Spectrum (60 Hz):

CH$_3$ at 104 and 119 Hz; aromatic ring at 417 to 455 Hz; COOH≃540 Hz.

EXAMPLE 9

6-chloro-4-phenyl-[4H]-1,3-benzodioxin-2-carboxylic acid

A solution of 30.1 g of 5-chloro-2-hydroxy-α-phenyl-benzene-methanol in 200 ml of anhydrous toluene was added dropwise with stirring at room temperature to a mixture of 10.35 g of sodium amide and 100 ml of toluene and the mixture was stirred for 2 hours at room temperature and was then refluxed for 6 hours. After cooling the mixture to room temperature, 22.3 g of potassium dichloroacetate were added thereto in small portions and 20 ml of hexamethylphosphoramide were added. The mixture was stirred for 20 hours at room temperature and was then refluxed for 4 hours and then returned to room temperature. 20 ml of ethyl acetate were added thereto followed by show addition of 250 ml of water and the aqueous phase containing the potassium salt of the desired acid was extracted 3 times with 100 ml of ether and acidified by bubbling sulfur dioxide therethrough. The mixture was then extracted 3 times with 100 ml of ether and the combined ether extracts were washed 3 times with 100 ml of water, dried over magnesium sulfate, treated with activated carbon and evaporated to dryness under reduced pressure. The 24 g of residue were effloresced in cyclohexane to obtain crystals which were crystallized from 520 ml of a 7–3 benzene-cyclohexane mixture to obtain 5.3 g of 6-chloro-4-phenyl-[4H]-1,3-benzodioxin-2-carboxylic acid melting at 194° C.

Analysis: $C_{15}H_{11}ClO_4$: Calculated: %C 61.97; %H 3.81; %Cl 12.20. Found: %C 62.2; %H 3.9; %Cl 12.1.

RMN Spectrum (60 Hz):

2- and 4-hydrogens at 343.5 and 364 Hz; COOH at ≃514 Hz; aromatic ring at 398 to 442.5 Hz.

EXAMPLE 10

6-chloro-4,4-diphenyl-[4H]-1,3-benzodioxin-2-carboxylic acid

A mixture of 12.4 g of 5-chloro-2-hydroxy-α,α-diphenyl-benzene methanol, 150 ml of toluene and 3.2 g of sodium amide was refluxed for 6 hours and was then cooled to room temperature after which 6.8 g of potassium dichloroacetate were added thereto. The mixture was refluxed for another 6 hours and was cooled to room temperature after which 300 ml of water were added thereto. The mixture was slowly acidified with N hydrochloric acid solution and was then made alkaline wiith a saturated sodium bicarbonate solution. The mixture was washed twice with 100 ml of methylene chloride and was then acidified with 2 N hydrochloric acid. The mixture was extracted 3 times with 100 ml of ether and the combined ether extracts were washed twice with 80 ml of water, dried over magnesium sulfate, treated with activated carbon and evaporated to dryness under reduced pressure. The 7 g of residue were crystallized from 300 ml of benzene to obtain 4.6 g of 6-chloro-4,4-diphenyl-[4H]-1,3-benzodioxin-2-carboxylic acid melting at 226° C.

Analysis: $C_{21}H_{15}ClO_4$: Calculated: %C 68.76; %H 4.12; %Cl 9.67. Found: %C 69.1; %H 4.3; %Cl 9.5.

RMN Spectrum (60 Hz):

2-hydrogen at 325 Hz; COOH at ≃313 Hz; aromatic ring 405 to 443 Hz.

EXAMPLE 11

A isomer of methyl 4-methyl-4-phenyl-[4H]-1,3-benzodioxin-2-carboxylate

A mixture of 1.3 g of 10% palladized activated carbon, 11.8 g of the A isomer of Example 2, 500 ml of ethanol and 10 ml of triethylamine was stirred in a hydrogenation cell under a hydrogen atmosphere at room temperature and was then filtered. The catalyst was washed with methylene chloride and the filtrate was evaporated to dryness under reduced pressure. The residue was taken up in 100 ml of water and 50 ml of 2 N hydrochloric acid solution were added thereto. The mixture was extracted 3 times with 150 ml of methylene chloride and the combined organic extracts were washed twice with 100 ml of water, dried over calcium chloride, treated with activated carbon and evaporated to dryness to obtain 9.7 g of the A isomer of methyl 4-methyl-4-phenyl-[4H]-1,3-benzodioxin-2-carboxylate. A sample crystallized from methanol melted at 124° C.

Analysis: $C_{17}H_{16}O_4$: Calculated %C 71.82; %H 5.67. Found: %C 72.1; %H 5.8.

RMN Spectrum (60 Hz):

2-hydrogen at 312 Hz; COOCH$_3$ at 231 Hz; CH$_3$ geminal to phenyl at 117 Hz; aromatic ring at 410 to 450 Hz.

EXAMPLE 12

A isomer of 4-methyl-4-phenyl-[4H]-1,3-benzodioxin-2-carboxylic acid

A mixture of 9.7 g of the A isomer of Example 11, 4 g of potassium hydroxide pastilles, 10 ml of water and 90 ml of methanol was stirred at room temperature for 16 hours and 400 ml of water were added thereto. The aqueous phase was washed twice with methylene chloride and was acidified with 2 N hydrochloric acid solution. The mixture was extracted three times with 150 ml of methylene chloride and the combined ether extracts were washed twice with 80 ml of water, dried over calcium chloride and evaporated to dryness under reduced pressure. The 8 g of residue were crystallized from a 2–8 ethyl acetate-cyclohexane mixture to obtain 5.1 g of the A isomer of 4-methyl-4-phenyl-[4H]-1,3-benzodioxin-2-carboxylic acid melting at 163° C.

Analysis: $C_{16}H_{14}O_4$: Calculated: %C 71.10; %H 5.22. Found: %C 71.1; %H 5.3.

RMN Spectrum (60 Hz):

CH$_3$ at 119 Hz; 2-hydrogen at 316 Hz; COOH at 534 Hz; aromatics at 418 to 450 Hz.

EXAMPLE 13

B isomer of methyl 4-methyl-4-phenyl-[4H]-1,3-benzodioxin-2-carboxylate 1.3 g of 10% palladized activated carbon, 12.8 g of the B isomer of Example 2, 10 ml of triethylamine and 200 ml of ethanol were stirred in a hydrogenation cell under hydrogen at room temperature for 2 hours and the mixture was filtered. The catalyst was rinsed with methylene chloride and the filtrate was evaporated to dryness under reduced pressure. The residue was taken up in 80 ml of water and 70 ml of 2 N hydrochloric acid were added thereto. The mixture was extracted 3 times with 100 ml of methylene chloride and the combined extracts were washed 3 times with 50 ml of water, dried over calcium chloride and evaporated to dryness under reduced pressure to obtain 10.2 g of the B isomer of methyl 4-methyl-4-phenyl-[4H]-1,3-benzodioxin-2-carboxylate. A sample of the product after crystallization from methanol melted at 137° C.

Analysis: $C_{17}H_{16}O_4$: Calculated: %C 71.82; %H 5.67. Found: %C 71.8; %H 5.8.

RMN Spectrum (60 Hz):

$CH_3$ at 128 Hz; $COOCH_3$ at 234 Hz; 2-hydrogen at 347 Hz; aromatics at 410 to 465 Hz.

EXAMPLE 14

B isomer of 4-methyl-4-phenyl-[4H]-1,3-benzodioxin-2-carboxylic acid

A mixture of 10.2 g of the B isomer of Example 13, 4 g of potassium hydroxide pastilles, 10 ml of water and 90 ml of methanol was stirred for 16 hours at room temperature and then 500 ml of water were added thereto. The aqueous phase was washed twice with 80 ml of methylene chloride and was acidified with 2 N hydrochloric acid solution. The mixture was extracted 3 times with 100 ml of methylene chloride and the combined organic extracts were washed twice with 80 ml of water, dried over calcium chloride and evaporated to dryness under reduced pressure to obtain 9 g of residue which was crystallized from a 2-8 ethyl acetate-cyclohexane mixture to obtain 6.7 g of B isomer of 4-methyl-4-phenyl-[4H]-1,3-benzodioxin-2-carboxylic acid melting at 153° C.

Analysis: $C_{16}H_{14}O_4$: Calculated: %C 71.10; %H 5.22. Found: %C 71.1; %H 5.3.

RMN Spectrum (60 Hz):

$CH_3$ at 128 Hz; 2-hydrogen at 348 Hz; aromatics at 410 to 460 Hz.

EXAMPLE 15 methyl 6-chloro-4,4-diphenyl-[4H]-1,3-benzodioxin-2-carboxylate

A mixture of 11 g of the product of Example 10, 50 g of Redex CF resin and 200 ml of methanol was refluxed with stirring for 16 hours and after cooling to room temperature, the mixture was vacuum filtered. The filter was rinsed with ether and the filtrate was evaporated to dryness under reduced pressure. The residue was taken up in 200 ml of ether and the ether phase was washed with 100 ml of a 5% sodium bicarbonate solution and then twice with 100 ml of water, was dried over magnesium sulfate, treated with activated carbon and evaporated to dryness to obtain 6.3 g of product which was crystallized from 140 ml of cyclohexane and dried to obtain 5.1 g of methyl 6-chloro-4,4-diphenyl-[4H]-1,3-benzodioxin-2-carboxylate melting at 172° C.

Analysis: $C_{22}H_{17}ClO_4$: Calculated: %C 69.38; %H 4.50; %Cl 9.31. Found: %C 69.7; %H 4.6; %Cl 9.3.

RMN Spectrum (60 Hz):

$COOCH_3$ at 230 Hz; aromatics at 406 to 443 Hz; 2-hydrogen at 324 Hz.

EXAMPLE 16

A isomer of ethyl 6-chloro-4-methyl-4-phenyl-[4H]-1,3-benzodioxin-2-carboxylate

STEP A: A isomer of 6-chloro-4-methyl-4-phenyl-[4H]-1,3-benzodioxin-2-carboxylic acid chloride A mixture of 4.9 g of the A isomer of Example 3 and 50 ml of benzene was stirred and cooled to 10° C. after which 2.3 ml of triethylamine were added dropwise. Then, a solution of 1.5 ml of thionyl chloride in 25 ml of anhydrous benzene was added thereto dropwise at 10° C. and the solution was refluxed for 2 hours and cooled to room temperature. The mixture was vacuum filtered and the resulting solution of the A isomer of 6-chloro-4-methyl-4-phenyl-[4H]-1,3-benzodioxin-2-carboxylic acid chloride was used for the next step.

STEP B: A isomer of ethyl 6-chloro-4-methyl-4-phenyl-[4H]-1,3-benzodioxin-2-carboxylate The solution of Step A was added dropwise at room temperature to a mixture of 3 ml of absolute ethanol, 50 ml of anhydrous benzene and 2.3 ml of triethylamine and the mixture was vacuum filtered. The filter was washed with cold benzene. The filtrate was washed twice with 40 ml of water, dried over calcium chloride, treated with activated carbon and evaporated to dryness under reduced pressure to obtain 9 g of residue which was crystallized from 30 ml of hexane and dried to obtain 4 g of the A isomer of ethyl 6-chloro-4-methyl-4-phenyl-[4H]-1,3-benzodioxin-2-carboxylate melting at 92° C.

Analysis: $C_{18}H_{17}ClO_4$: Calculated: %C 64.97; %H 5.15; %Cl 10.65. Found: %C 65.1; %H 5.3; %Cl 10.8.

RMN Spectrum (60 Hz):

$CH_3$ of $C_2H_5$ at 72.5–79.5-87 Hz; 4-$CH_3$ at 116 Hz; $CH_2$ of $CH_2$—$CH_3$ at 247.5-255-262-269 Hz; 2-hydrogen at 308 Hz; aromatics at 412 to 441 Hz.

EXAMPLE 17

A isomer of sodium 6-chloro-4-methyl-4-phenyl-[4H]-1,3-benzodioxin-2-carboxylate 4.6 g of the A isomer of Example 3 was added at room temperature to a mixture of 0.6 g of sodium hyroxide in 250 ml of absolute ethanol and the mixture was refluxed for 5 minutes and was then filtered and cooled to room temperature. 500 ml of ether were added to the filtrate and the mixture was stirred for 16 hours at room temperature and was filtered. The recovered precipitate was dried to obtain 3.8 g of the A isomer of sodium 6-chloro-4-methyl-4-phenyl-[4H]-1,3-benzodioxin-2-carboxylate melting at 160° C.

Analysis: $C_{16}H_{12}ClO_4Na$: Calculated: %C 58.82; %H 3.70; %Cl 10.85. Found: %C 58.5; %H 3.8; %Cl 10.7.

EXAMPLE 18 d and l isomers of the A isomer of 6-chloro-4-methyl-4-phenyl-[4H]-1,3-benzodioxin-2-carboxylic acid STEP A: 1-p-nitrophenyl-2-amino-1,3-propanediol salt of l-isomer of the A isomer of 6-chloro-4-methyl-4-phenyl-[4H]-1,3-benzodioxin-2-carboxylic acid A mixture of 15.2 g of the A isomer of Example 3, 16.2 g of 1-p-nitrophenyl-2-amino-1,3-propanediol and 800 ml of ethyl acetate was refluxed until 5 minutes after precipitation of a salt and the mixture was cooled to room temperature and was vacuum filtered. The recovered precipitate was rinsed with ethyl acetate and was dried under reduced pressure to obtain 10 g of raw product. The mother liquors were savid for recovery of the raw d-isomer later on. The 10 g of product were crystallized from isopropanol to obtain 6.4 g of the 1-p-nitrophenyl-2-amino-1,3-propanediol salt of l-isomer of the A isomer of 6-chloro-4-methyl-4-phenyl-[4H]-1,3-benzodioxin-2-carboxylic acid melting at 218° C. and having a specific rotation of $[\alpha]_D^{20} = -84° \pm 2°$ (c=1% in ethanol). A sample was crystallized from isopropanol and melted at 218° C. and had a specific rotation $[\alpha]_D^{20} = -84.5° \pm 2°$ (c=1% in ethanol).

STEP B: 1-isomer of the A isomer of 6-chloro-4-methyl-4-phenyl-[4H]-1,3-benzodioxin-2-carboxylic acid A suspension of the salt of Step A in 150 ml of N hydrochloric acid was extracted 3 times with 75 ml of ether and the combined organic extracts were washed 3 times with water, were dried over magnesium sulfate and evaporated to dryness under reduced pressure to obtain 3.5 g of raw product which was crystallized from cyclohexane to obtain 2.7 g of crystals. The said product was crystallized from cyclohexane to obtain 2.3 g of crystals melting at 113°–114° C. then recrystallizing and melting at 128° C. The product was again crystallized from 80 ml of cyclohexane to obtain 1.8 g of a product melting at 113° C. 0.5 g of product was recovered from the mother liquors of the crystallizations. The two products were combined and crystallized from 50 ml of refluxing cyclohexane over 20 minutes to obtain 2 g of the 1-isomer of the A-isomer of 6-chloro-4-methyl-4-phenyl-[4H]-1,3-benzodioxin-2-carboxylic acid melting at 140° C. and a specific rotation $[\alpha]_D^{20} = 157° \pm 2.5°$ (c=1% in 95 ethanol). The differences in melting points is probably due to variations in crystals structure.

Analysis: $C_{16}H_{13}ClO_4$: Calculated: %C 63.06; %H 4.30; %Cl 11.63. Found: %C 63.2; 10H 4.4; %Cl 11.6.

RMN Spectrum (deuterchloroform-60 Hz):

$CH_3$ at 116.5 Hz; 2-hydrogen at 313 Hz; aromatics at 415 to 443 Hz; OH at about 540 Hz.

d-isomer

STEP A: raw d isomer of 6-chloro-4-methyl-4-phenyl-[4H]-1,3-benzodioxin-2-carboxylic acid The ethyl acetate mother liquors from the above salification were evaporated to dryness under reduced pressure to obtain 17.8 g of raw product which was taken up in 200 ml of 2 N hydrochloric acid. The mixture was extracted 3 times with 100 ml of ether and the combined organic phases were washed twice with 50 ml of water, dried over magnesium sulfate and evaporated to dryness under reduced pressure to obtain 8.4 g of residue. The residue was taken up in 150 ml of a 7-3 cyclohexane-ethyl acetate mixture which was refluxed and cooled. The mixture was vacuum filtered to remove residual starting racemic acid and the filtrate was evaporated to dryness under reduced pressure to obtain 7 g of raw d-isomer of the A isomer of 6-chloro-4-methyl-4-phenyl-[4H]-1,3-benzodioxin-2-carboxylic acid.

STEP B: dl-p-nitrophenyl-2-amino-1,3-propanediol salt of the d-isomer of 6-chloro-4-methyl-phenyl-[4H]-1,3-benzodioxin-2-carboxylic acid The residue of the preceding step in 300 ml of ethyl acetate was admixed with 7.4 g of dl-p-nitrophenyl-2-amino-1,3-propanediol. The suspension was refluxed and then cooled and after precipitation of the salt at room temperature, the mixture was vacuum filtered. The recovered precipitate was rinsed with ethyl acetate and was dried to obtain 11.4 g of product melting at 200° C. The product was crystallized from 1.1 liters of isopropanol to obtain 6.2 g of product melting at 218° C. which was crystallized from 800 ml of isopropanol to obtain 5 g of dl-p-nitrophenyl-2-amino-1,3-propanediol salt of the d-isomer of 6-chloro-4-methyl-4-phenyl-[4H]-1,3-benzodioxin-2-carboxylic acid melting at about 218° C.

STEP C: d-isomer of the A isomer of 6-chloro-4-methyl-4-phenyl-[4H]-benzodioxin-2-carboxylic acid The salt from Step B was dissolved in 150 ml of water and the solution was acidified with 2 N hydrochloric acid and was extracted twice with 100 ml of ether. The ether extracts were washed twice with 50 ml of water, dried over magnesium sulfate and evaporated to dryness under reduced pressure. The 2.9 g of residue were dissolved in a 2-8 ethyl ether-petroleum ether (b.p. =60°−80° C.) mixture to finally obtain 2.4 g of the d-isomer of the A isomer of 6-chloro-4-methyl-4-phenyl-[4H]-1,3-benzodioxin-2-carboxylic acid with a melting point of 128° C. and a specific rotation of $[\alpha]_D^{20} = +153° \pm 2.5°$ (c=1% in ethanol). After crystallization from 100 ml of cyclohexane, the 2 g of product melted at 128° C. and had the same specific rotation. After crystallization from 60 ml of cyclohexane, the 1.7 g of product melted at 140° C. and a specific rotation of $[\alpha]_D^{20} = +154.5° \pm 2.5°$ (c=1% in ethanol). The difference in melting points was probably due to different crystal structure.

Analysis: $C_{16}H_{13}ClO_4$: Calculated: %C 63.06; %H 4.30; %Cl 11.63. Found: %C 63.2; %H 4.3; %Cl 11.6.

RMN Spectrum (deuterochloroform-60 Hz):

$CH_3$ at 117 Hz; monosubstituted phenyl at 440 Hz; aromatics at 413 to 440 Hz; OH at 485 Hz; 2-hydrogen at 312.5 Hz.

EXAMPLE 19

6-chloro-4-methyl-4-(3-chlorophenyl)-[4H]-1,3-benzodioxin-2-carboxylic acid (mixture of two racemates diastereoisomers)

STEP A: 4-chlorophenyl 3-chloro-benzoate

A solution of 80 g of 3-chlorophenyl-carboxylic acid chloride in 100 ml of anhydrous benzene was added dropwise with stirring at 10° C. to a mixture of 5.87 g of 4-chlorophenol, 46.1 g of triethylamine and 250 ml of anhydrous benzene and the mixture was stirred overnight at room temperature. The mixture was vacuum filtered and the filtrate was evaporated to dryness to obtain 122 g of raw product which was crystallized from 200 ml of a 2-8 ethyl ether-petroleum ether (b.p.=60°-80° C.) mixture to obtain 116 g of 4-chlorophenyl 3-chlorobenzoate melting at 72° C.

Analysis: $C_{13}H_8Cl_2O_2$: Calculated: %C 58.45; %H 3.02; %Cl 26.55. Found: %C 58.5; %H 3.0; %Cl 26.2.

STEP B: [5-chloro-2-hydroxyphenyl]-[3-chlorophenyl]-methanone

A mixture of 64.5 g of the product of Step A and 32 g of aluminum chloride was progressively heated with stirring up to 160° C. which temperature was held for 30 minutes and the mixture was cooled to room temperature. The product was dissolved in methylene chloride and 250 ml of N hydrochloric acid were slowly added thereto. The organic phase was decanted and the aqueous phase was extracted twice with 70 ml of methylene chloride. The organic extracts were washed 3 times with 70 ml of water, dried over calcium chloride and evaporated to dryness under reduced pressure to obtain 60 g of residue which was crystallized from a 2-8 ethyl ether-petroleum ether (b.p.=60°-80° C.) mixture. The product was vacuum filtered and dried to obtain 41.3 g of [5-chloro-2-hydroxyphenyl]-[3-chlorophenyl]-methanone. Recrystallization from cyclohexane gave a product melting at 72° C.

Analysis: $C_{13}H_8Cl_2O_2$: Calculated: %C 58.45; %H 3.02; %Cl 26.55. Found: %C 58.4; %H 3.2; %Cl 26.5.

STEP C: 1-[5-chloro-2-hydroxyphenyl]-1-[3-chlorophenyl]ethanol

A solution of 64 g of methyl iodide in 100 ml of anhydrous ether was added dropwise with stirring at room temperature to a dispersion of 11 g of magnesium turnings in 100 ml of anhydrous ether. The mixture was reached reflux during the addition and reflux was maintained for one hour after which the mixture was cooled to room temperature. A solution of 31.7 g of the product of Step B in 150 ml of anhydrous benzene and 100 ml of anhydrous ether was added dropwise thereto over 20 minutes and then in the ether was distilled and 250 ml of anhydrous benzene were added thereto. The mixture was refluxed for 4 hours and was cooled to room temperature. The mixture was placed into an ice bath and N hydrochloric acid was added thereto to effect hydrolysis. The organic phase was decanted and the aqueous phase was extracted twice with 80 ml of ether. The combined ether extracts were washed 3 times with 80 ml of water, dried over magnesium sulfate and evaporated to dryness under reduced pressure. The 31.5 g of residue was crystallized from 750 ml of cyclohexane to obtain 25.5 g of 1-[5-chloro-2-hydroxyphenyl]-1-[3-chlorophenyl]-ethanol melting at 125° C.

Analysis: $C_{14}H_{12}Cl_2O_2$: Calculated: %C 59.38; %H 4.27; %Cl 25.04. Found: %C 59.2; %H 4.3; %Cl 24.9.

STEP D: 6-chloro-4-methyl-4-(3-chlorophenyl)-[4H]-1,3-benzodioxin-2-carboxylic acid (mixture of two racemates diastereoisomers A suspension of 28.3 g of the product of Step C in 250 ml of toluene was added in small particles with stirring at room temperature to a mixture of 10 g of sodium amide and 200 ml of anhydrous toluene and the mixture was refluxed for 6 hours during which 1 g of sodium amide was added. The mixture was cooled to room temperature and 25 g of potassium dichloroacetate were added thereto in small portions. The mixture was refluxed for another 6 hours and was cooled to room temperature and 150 ml of water were slowly added thereto followed by the addition of 150 ml of 2 N hydrochloric acid. The organic phase was decanted and the aqueous phase was extracted twice with 100 ml of ether. The combined organic phases were washed twice with 100 ml of water and were extracted once with a saturated sodium bicarbonate solution and twice with 100 ml of water. The aqueous extracts were washed 3 times with 100 ml of ether and was slowly acidified with 2 N hydrochloric acid. The aqueous phase was extracted 3 times with 150 ml of ether and the combined ether extracts were washed twice with 75 ml of water, treated with activated carbon, dried over magnesium sulfate and evaporated to dryness under reduced pressure to obtain 29.3 g of 6-chloro-4-methyl-4-(3-chlorophenyl)-[4H]-1,3-benzodioxin-2-carboxylic acid (mixture of two racemates diastereoisomers).

RMN Spectrum (deuterechloroform-60 Hz):
$CH_3$ at 117 and 125.5 Hz; 2-hydrogen at 315.5 and 346 Hz; aromatics at 412 to 455 Hz; COOH at 588 Hz.

EXAMPLE 20

A and B isomers of methyl 6-chloro-4-methyl-4-(3-chlorophenyl)-[4H]-1,3-benzodioxin-2-carboxylate A mixture of 29.3 g of the product of Example 19, 300 ml of methanol and 30 g of a strong sulfonic acid cationic resin was refluxed with stirring for 20 hours and after cooling to room temperature, the mixture was vacuum filtered. The filter was rinsed with methanol and the filtrate was evaporated to dryness under reduced pressure. The 20 g of residue were chromatographed over a pressurized column of silica gel and was fractionally eluted with a 2–8 ethyl ether-petroleum ether (b.p.=60° to 80° C.) mixture to obtain after evaporation of the solvent 9.5 g of the A isomer and 8.4 g of the B isomer of methyl 6-chloro-4-methyl-4-(3-chlorophenyl)-[4H]-1,3-benzodioxin-2-carboxylate. Crystallization of 4 g of the A isomer from methanol yielded 3.2 g of A isomer melting at 112° C.

A isomer Analysis: $C_{17}H_{13}Cl_2O_4$: Calculated: %C 57.97; %H 3.72; %Cl 20.13. Found: %C 57.9; %H 4.0; %Cl 19.8.

RMN Spectrum (deuterochloroform-90 Hz):
$CH_3$ at 172 Hz; $COOCH_3$ at 345 Hz; 2-hydrogen at 461.5 Hz; aromatics at 623 to 660 Hz. and 8,4 g B isomer in the form of crude product.

B isomer Analysis: $C_{17}H_{13}Cl_2O_4$: Calculated: %C 57.97; %H 3.72; %Cl 20.13. Found: %C 58.2; %H 4.0; %Cl 20.1.

RMN Spectrum (deuterochloroform-90 Hz):
$CH_3$ at 184 Hz; $COOCH_3$ at 343.5 Hz; 2-hydrogen at 509 Hz; aromatics at 612 to 674 Hz.

EXAMPLE 21

A isomer of 6-chloro-4-methyl-4-(3-chlorophenyl)-[4H]-1,3-benzodioxin-2-carboxylic acid A mixture of 6.5 g of the A isomer of Example 20, 2.8 g of potassium hydroxide pastilles, 10 ml of water and 100 ml of methanol was stirred for 16 hours at room temperature and 200 ml of water. The aqueous solution was washed tice with 50 ml of ether and was then acidified with 2 N hydrochloric acid. The aqueous phase was extracted 3 times with 80 ml of ether and the combined ether extracts were washed twice with 50 ml of water, dried over magnesium sulfate and evaporated to dryness under reduced pressure to obtain 6.1 g of residue which was crystallized from 100 ml of cyclohexane to obtain 3.6 g of the A isomer of 6-chloro-4-methyl-4-(3-chlorophenyl)-[4H]-1,3-benzodioxin-2-carboxylic acid melting at 131° C.

Analysis: $C_{16}H_{12}Cl_2O_4$: Calculated: %C 56.66; %H 3.57; %Cl 20.90. Found: %C 56.7; %H 3.7; %Cl 20.6.

RMN Spectrum (deuterochloroform-60 MHz):
$CH_3$ at 174.5 Hz; 2-hydrogen at 466.5 Hz; aromatic peaks at 625 to 665 Hz.

EXAMPLE 22

B isomer of 6-chloro-4-methyl-4-(3-chlorophenyl)-[4H]-1,3-benzodioxin-2-carboxylic acid A mixture of 5.3 g of isomer B of Example 20, 2.4 g of potassium hydroxide pastilles, 10 ml of water and 100 ml of methanol was stirred overnight at room temperature and 250 ml of water were added thereto. The aqueous phase was washed twice with 80 ml of ether and was acidified with 2 N hydrochloric acid. The aqueous phase was extracted 3 times with 80 ml of ether and the combined organic phases were washed twice with 50 ml of water, dried over magnesium sulfate and evaporated to dryness under reduced pressure. The 5.3 g of residue was crystallized from 110 ml of a 8-3 cyclohexaneethyl acetate mixture to obtain 4 g of the B isomer of 6-chloro-4-methyl-4-(3-chlorophenyl)-[4H]-1,3-benzodioxin-2-carboxylic acid melting at 177° C.

Analysis: $C_{16}H_{12}Cl_2O_4$: Calculated: %C 56.66; %H 3.87; %Cl 20.90. Found: %C 56.8; %H 3.8; %Cl 20.9.
RMN Spectrum (Deuterochloroform-90 MHz):
$CH_3$ at 185.5 Hz; 2-hydrogen at 510 Hz; aromatics at 610 to 673 Hz.

EXAMPLE 23

6-chloro-4-isopropyl-1-phenyl-[4H]-1,3-benzodioxin-2-carboxylic acid (mixture of two racemates diasteroisomers).

STEP A: 5-chloro-α-[isopropyl]-2-hydroxy-α-phenyl-benzenemethanol

A mixture of 21.4 g of magnesium turnings, 200 ml of anhydrous ether and 2 ml of isopropyl bromide was stirred until the magnesium was in the desired form and a solution of 110.8 g of isopropyl bromide in 400 ml of anhydrous ether was added dropwise thereto to keep a slight reflux and room temperature. The mixture was then refluxed for 2 hours and 520 ml of the resulting solution were added dropwise at room temperature to a mixture of 58.2 g of [5-chloro-2-hydroxyphenyl]-phenyl-methanone in 600 ml of anhydrous benzene. The ether was distilled and progressively was replaced with benzene and the mixture was refluxed for 6 hours and was then cooled to room temperature. The reaction mixture was poured into a liter of iced 10% ammonium chloride solution and the organic phase was decanted. The aqueous phase was extracted twice with 150 ml of ether and the combined ether extracts were washed 3 times with 100 ml of water, dried, treated with activated carbon and evaporated to dryness under reduced pressure. The 74 g of residue were chromatographed over silica gel and was eluted with methylene chloride to obtain a fraction of 18 g of product which was crystallized from 50 ml of cyclohexane to obtain 8.7 g of 5-chloro-α-isopropyl-2-hydroxy-α-phenyl-benzene-methanol melting at 114° C. After crystallization from cyclohexane, the product melting at 115° C.

Analysis: $C_{18}H_{17}ClO_2$: Calculated: %C 69.43; %H 6.19; %Cl 12.81. Found: %C 69.7; %H 6.2; %Cl 12.8.
RMN Spectrum (deuterochloroform-60 MHz):
2-$CH_3$ of isopropyl at 48-55 Hz and 63-70 Hz; >CH— at 165 Hz (multiplet) at 165 Hz; OH of 2-hydroxy at 537 Hz; aromatics at 395–455 hz.

STEP B: racemic 6-chloro-4-isopropyl-4-phenyl-[4H]-1,3-benzodioxin-2-carboxylic acid A solution of 3.66 ml of dichloroacetic acid in 60 ml of anhydrous dioxane was added over 10 minutes with stirring at room temperature to a mixture of 8.1 g of sodium hydride as a 50% oil suspension, 60 ml of anhydrous dioxane and 360 ml of dibenzo-18-couronne-6- [type described in Synthesis, 1976, p. 168] and then a mixture of 8.7 g of the product of Step A in 30 ml of anhydrous dioxane was added thereto at room temperature. The mixture was heated for 10 hours at 90°–100° C. and was cooled to room temperature. 500 ml of water were added dropwise to the solution in an ice water bath and the aqueous phase was washed twice with 200 ml of ether. The ether extracts were extracted 3 times with 100 ml of 2 N sodium hydroxide and the aqueous phase was acidified with 2 N hydrochloric acid and was extracted 3 times with 150 ml of ether. The combined ether phase were washed 3 times with 100 ml of water and was then extracted with a saturated sodium bicarbonate solution and then 3 times with 100 ml of water. The aqueous phase was washed twice with 80 ml of ether and was acidified with 2 N hydrochloric acid. The aqueous phase was extracted 3 times with 150 ml of ether and the combined ether phases were washed 3 times with 80 ml of water, dried, treated with activated carbon and evaporated to dryness to obtain 8.8 g of 6-chloro-4-isopropyl-4-phenyl-[4H]-1,3-benzodioxin-2-carboxylic acid (mixture of two racemates diastereoisomers) in the form of an oil.

RMN Spectrum (deuterochloroform-60 MHz):
2-hydrogen at 323 Hz (peak of A isomer); 2-hydrogen at 335 Hz (peak of B isomer); two $CH_3$ of isopropyl at 49 to 69 Hz; hydrogen of isopropyl at 100 to 190 Hz; aromatics at 410 to 465 Hz; OH at 490 Hz.

EXAMPLE 24

A isomer of methyl 6-chloro-4-isopropyl-4-phenyl-[4H]-1,3-benzodioxin-2-carboxylate STEP A: isomer A of 6-chloro-4-isopropyl-4-phenyl-[4H]-1,3-benzodioxin-2-carboxylic acid chloride A mixture of 8.8 g of the product of Example 23 in 100 ml of anhydrous benzene was stirred at room temperature while 3.7 ml of triethylamine, 3.8 ml of thionyl chloride and 25 ml of anhydrous benzene were added thereto and the mixture was refluxed for 2 hours and was cooled to room temperature. The mixture was vacuum filtered and the filter was washed with a little anhydrous benzene. The filtrate containing the A isomer of 6-chloro-4-isopropyl-4-phenyl-[4H]-1,3-benzodioxin-2-carboxylic acid chloride which was used for the next step.

STEP B: A isomer of methyl 6-chloro-4-isopropyl-4-phenyl[4H]-1,3-benzodioxin-2-carboxylate The solution of Step A was added dropwise with stirring at room temperature to a mixture of 50 ml of anhydrous benzene, 4 ml of anhydrous methanol and 3.7 ml of triethylamine and the mixture was stirred at room temperature for 50 hours and then vacuum filtered. The filter was washed with a little benzene and the filtrate was washed with 2 N sodium hydroxide solution and then water until the wash waters were neutral. The organic phase was dried, treated with activated carbon and evaporated to dryness to obtain 7.3 g of residue which was crystallized from methanol. The mixture was vacuum filtered and the crystals were dried to obtain 4.5 g of product which was crystallized from methanol to obtain 1.8 g of the A isomer of methyl 6-chloro-4-isopropyl-4-phenyl-[4H]-1,3-benzodioxin-2-carboxylate melting at 114°–115° C.

Analysis: $C_{19}H_{19}ClO_4$: Calculated: %C 65.80; %H 5.52; %Cl 10.22; Found: %C 65.8; %H 5.6; %Cl 10.2.
RMN Spectrum (deuterochloroform-90 MHz):
2 $CH_3$ of isopropyl at 74 and 77 Hz; >CH— radical of isopropyl at 187 to 239 Hz; $COOCH_3$ at 351 Hz; 2-hydrogen at 479 Hz; aromatic peaks at 616 to 681 Hz.

EXAMPLE 25

6-chloro-4-tert.-butyl-4-phenyl-[4H]-1,3-benzodioxin-2-carboxylic acid (mixture of two racemates diastereoisomers)

STEP A: 5-chloro-α-tert.-butyl-2-hydroxy-α-phenyl-benzenemethanol 192 g of a solution of tert.-butyllithium in pentane was added dropwise at room temperature to a mixture of 40.2 g of (5-chloro-2-hydroxy-phenyl)-phenyl-mthanone and 400 ml of anhydrous ether and the mixture was stirred for 2 hours at room temperature. The ethanol was distilled with progressive addition of 600 ml of anhydrous benzene and was then refluxed for 16 hours and cooled to room temperature. The mixture was poured into one liter of iced 10% ammonium chloride solution and the organic phase was decanted. The aqueous phase was extracted twice with 100 ml of ether and the combined ether extracts were washed twice with 70 ml of water, dried over magnesium sulfate, treated with activated carbon and evaporated to dryness. The 50 g of oil residue was chromatographed over silica gel and eluted with methylene chloride to obtain 14.1 g of 5-chloro-α-tert.-butyl-2-hydroxy-α-phenyl-benzenemethanol which melted at 146° C. after crystallization from cyclohexane.

Analysis: $C_{17}H_{19}ClO_2$:

Calculated: %C 70.22; %H 6.59; %Cl 12.19. Found: %C 70.5; %H 6.7; %Cl 11.9.

RMN Spectrum (deuterochloroform-60 MHz):

2-OH at 530 Hz; methanol OH at 175 Hz; tert.butyl at 75 Hz; aromatic of phenyl α to methanol at 420 to 455 Hz; other aromatic at 400 to 455 Hz.

A solution of 5.82 ml of dichloroacetic acid in 100 ml of dioxane was added dropwise with stirring to a mixture of 12.8 g of sodium hydride in a 50% oil suspension, 100 ml of anhydrous dioxane and 600 mg of dibenzo-18-couronne-6 kept at room temperature and a solution of 14.1 g of 5-chloro-2-tert.-butyl-2-hydroxy-α-phenyl-benzene-methanol in 100 ml of dioxane was added dropwise at room temperature. The mixture was heated at 80° C. for 6 hours and was then cooled to room temperature which was kept on an ice bath. 400 ml of water were added and the aqueous phase was extracted with 600 ml of ether. The ether extract was extracted 3 times with 100 ml of 0.1 N sodium hydroxide solution and the aqueous phase was acidified with 2 N hydrochloric acid and was extracted 3 times with 150 ml of ether. The organic extracts were washed 3 times with 100 ml of water and were extracted with a saturated sodium bicarbonate solution and then 3 times with 100 ml of water. The combined aqueous phases were washed 3 times with ether and was acidified with 2 N hydrochloric acid. The aqueous phase was extracted 4 times with 150 ml of ether and the ether phases were washed 3 times with water, dried over magnesium sulfate, treated with activated carbon and evaporated to dryness to obtain 9.1 g of raw 6-chloro-4-tert.-butyl-4-phenyl-[4H]-1,3-benzodioxin-2-carboxylic acid (mixture of two racemates diastereoisomers).

RMN Spectrum (deuterochloroform-60 MHz):

2-hydrogen at 317 Hz (A isomer); 2-hydroxy at 340 Hz (B isomer); tert.-butyl at 63 and 65 Hz; aromatics at 415 to 472 Hz; OH at 527 Hz.

EXAMPLE 26

A isomer of methyl 6-chloro-4-tert.-butyl-4-phenyl-[4H]-1,3-benzodioxin-2-carboxylate STEP A: 6-chloro-4-tert.-butyl-4-phenyl-[4H]-1,3-benzodioxin-2-carboxylic acid chloride (mixture of two racemates diastereoisomers)

3.7 ml of triethylamine were added progressively at room temperature to a mixture of 9.1 g of the product of Example 25 in 100 ml of anhydrous benzene and then a solution of 6.2 g of thionyl chloride in 25 ml of anhydrous benzene was added thereto dropwise. The mixture was refluxed for 3 hours, cooled to room temperature and was vacuum filtered. The precipitate was washed with anhydrous benzene and the filtrate was concentrated under reduced pressure to 30 ml of a solution containing 6-chloro-4-tert.-butyl-4-phenyl-[4H]-1,3-benzodioxin-2-carboxylic acid chloride for the next step (mixture of two racemates diastereoisomers).

STEP B: A isomer of methyl 6-chloro-4-tert.-butyl-4-phenyl-[4H]-1,3-benzodioxin-2-carboxylate The solution of Step A was added dropwise at 15°-20° C. to a stirred mixture of 3 ml of methanol, 50 ml of anhydrous benzene and 3.7 ml of triethylamine and the mixture was stirred for 16 hours at room temperature and was vacuum filtered. The filter was washed with anhydrous benzene and the filtrate was evaporated to dryness under reduced pressure. The 6.5 g of residue was chromatographed over silica gel and were eluted with a 2-8 ethyl ether-petroleum ether (b.p. = 60°–80° C.) mixture. The solvent was evaporated and the residue was crystallized from 20 ml of methanol and was dried to obtain the A isomer of methyl 6-chloro-4-tert.-butyl-4-phenyl-[4H]-1,3-benzodioxin-2-carboxylate melting at 85° C.

Analysis: $C_{20}H_{21}ClO_4$: Calculated: %C 66.57; %H 5.87; %Cl 9.82. Found: %C 66.5; %H 6.0; %Cl 10.0.

RMN Spectrum (deuterochloroform-60 MHz):

tert.-butyl at 62 Hz; COOCH$_3$ at 117 Hz; 2-hydrogen at 338 Hz; aromatic peaks at 412 to 468 Hz.

EXAMPLE 27

6-fluoro-4-methyl-4-phenyl-[4H]-1,3-benzodioxin-2-carboxylic acid (mixture of two racemates diastereoisomers)

STEP A: α-phenyl-α-methyl-(5-fluoro-2-hydroxy)-phenyl-methanol

A mixture of 13.3 g of magnesium turnings and 50 ml of anhydrous ether was stirred under an argon atmosphere and then a solution of 34.7 ml of methyl iodide in 250 ml of anhydrous ether was slowly added thereto. The mixture was refluxed for one hour and 220 ml of the resulting magnesium solution were added to a solution of 30 g of α-phenyl-(5-fluoro-2-hydroxy)-phenyl-methanone in 150 ml of anhydrous benzene. The ether was distilled while being replaced with anhydrous benzene and was then stirred for 4 hours at about 78° C. and was then cooled. The mixture was poured into an ammonium chloride solution and the mixture was extracted with ether. The ether extracts were washed with water, dried over magnesium sulfate and evaporated to dryness under reduced pressure to obtain 32 g of raw α-phenyl-α-methyl-(5-fluoro-2-hydroxy)phenyl-methanol. A sample crystallized from cyclohexane melted at 122° C.

Analysis: $C_{14}H_{13}FO_2$: Calculated: %C 72.40; %H 5.64; %F 8.18. Found: %C 72.4; %H 5.6; %F 8.2.

STEP B: 6-fluoro-4-methyl-4-phenyl-[4H]-1,3-benzodioxin-2-carboxylic acid (mixture of two racemates diastereoisomers)

A solution of 16.5 g of dichloroacetic acid in 150 ml of dioxane was added over one hour under an argon atmosphere to a mixture of 25 g of sodium hydride, 350 ml of anhydrous dioxane and 1.55 g of dibenzo-18-couronne-6 and after the end of the reaction, a solution of 31 g of the product of Step A in 150 ml of anhydrous dioxane was added thereto over one hour. The mixture was stirred at 80°-85° C. for 6 hours, was cooled and was then poured into a water-ice mixture. The mixture was extracted with ether and the aqueous phase was acidified and again extracted with ether. The latter ether phase was washed with water and was extracted with a sodium bicarbonate solution. The aqueous phase was washed with methylene chloride and acidified. The aqueous phase was extracted with methylene chloride and the organic extracts were washed with water, dried over magnesium sulfate and evaporated to dryness under reduced pressure to obtain 29.5 g of raw 6-fluoro-4-methyl-4-phenyl-[4H]-1,3-benzodioxin-2-carboxylic acid (mixture of two racemates diastereoisomers) in the form of an oil.

RMN Spectrum (deuterochloroform-60 MHz):
2-hydrogen at 310 Hz and CH₃ at 117 Hz (A isomer); 2-hydrogen at 339 Hz and CH₃ at 126 Hz (B isomer); aromatic at 400 to 450 Hz; OH at 505 Hz.

EXAMPLE 28

A isomer of methyl 6-fluoro-4-methyl-4-phenyl-[4H]-1,3-benzodioxin-2-carboxylate A mixture of 29.5 g of the product of Example 27, 300 ml of methanol and 130 g of acid resin was refluxed for 24 hours, was cooled, treated with activated carbon and was filtered. The filtrate was rinsed with methanol and the filtrate was dried. The residue was taken up in ether and the ether phase was washed three times with 200 ml of sodium bicarbonate solution and then with water, was dried over magnesium sulfate and evaporated to dryness under reduced pressure. The 23.8 g of residue was taken up in 200 ml of methanol and 5 g of the product were crystallized from 20 ml of methanol to obtain 4.4 g of the A isomer of methyl 6-fluoro-4-methyl-4-phenyl-[4H]-1,3-benzodioxin-2-carboxylate melting at 95° C.

Analysis: $C_{17}H_{15}FO_4$: Calculated: %C 67.54; %H 5.00; %F 6.28. Found: %C 67.7; %H 5.0; %F 6.2.

RMN Spectrum (deuterochloroform-90 MHz):
CH₃ at 171 Hz; COOCH₃ at 345 Hz; 2-hydrogen at 463 Hz; aromatic peaks at 615 to 680 Hz.

EXAMPLE 29

A isomer of (2,2-dimethyl-1,3-dioxolan-4-yl)-methyl 6-chloro-4-methyl-4-phenyl-[4H]-1,3-benzodioxin-2-carboxylate STEP A: A isomer of 6-chloro-4-methyl-4-phenyl-[4H]-1,3-benzodioxin-2-carboxylic acid chloride 1.66 g of triethylamine was added dropwise at 10° C. with stirring to a mixture of 4.9 g of the A isomer of Example 3 and 50 ml of anhydrous benzene and then a solution of 2.5 g of thionyl chloride in 25 ml of anhydrous benzene was added dropwise at 10° C. The mixture was refluxed for 2 hours, cooled to room temperature and vacuum filtered. The filtrate containing the A isomer of 6-chloro-4-methyl-4-phenyl-[4H]-1,3-benzodioxin-2-carboxylic acid chloride was used for the next step.

STEP B: A isomer of (2,2-dimethyl-1,3-dioxolan-4-yl)-methyl 6-chloro-4-methyl-4-phenyl-[4H]-1,3-benzodioxin-2-carboxylate The filtrate of Step A was added dropwise at room temperature with stirring to a mixture of 2.25 g of (2,2-dimethyl-1,3-dioxolan-4-yl)-methanol, 50 ml of anhydrous benzene and 2.3 ml of triethylamine and the mixture was stirred for 20 hours at room temperature and was filtered. The filtrate was washed with 10% sodium bicarbonate solution and then with water until the wash water was neutral, was dried over calcium chloride, treated with activated carbon and evaporated to dryness. The residue of 4.5 g was chromatographed over silica gel and was eluted with methylene chloride to obtain 2 g of raw A isomer of (2,2-dimethyl-1,3-dioxolan-4-yl)-methyl 6-chloro-4-methyl-4-phenyl-[4H]-1,3-benzodioxin-2-carboxylate in the form of a colorless gum.

Analysis: $C_{22}H_{23}ClO_6$: Calculated: %C 63.08; %H 5.53; %Cl 8.45. Found: %C 63.0; %H 5.5; %Cl 8.9.

RMN Spectrum (deuterochloroform-60 MHz):
CH₃ of 2,2-dimethyl-dioxolan at 81–82 Hz; 4-CH₃ at 115 Hz;

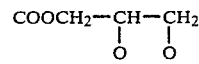

at 215 to 260 Hz; aromatics at 411 to 441 Hz.

EXAMPLE 30

A isomer of 2-(diethylamino)-ethyl 6-chloro-4-methyl-4-phenyl-[4H]-1,3-benzodioxin-2-carboxylate hydrochloride A mixture of 6.2 g of the A isomer of Example 16, 100 ml of anhydrous toluene, 2.6 g of dimethylamino ethanol and a very small amount of sodium hydride was refluxed with stirring under a nitrogen atmosphere for 3 hours and was cooled. 5 ml of 4 N hydrochloric acid in ether were added thereto followed by the addition of 200 ml of anhydrous ether and the mixture was filtered. The filtrate was washed with ether and evaporated to dryness. The residue of 3.7 g was taken up in 20 ml of isopropanol at 60° C. and the solution was treated with activated carbon, cooled and 50 ml of ether added thereto. The mixture was filtered and the product was dried to obtain 2.7 g of the A isomer of 2-(diethylamino)ethyl 6-chloro-4-methyl-4-phenyl-[4H]-1,3-benzodioxin-2-carboxylate hydrochloride melting at 110° C.

Analysis: $C_{22}H_{27}Cl_2NO_4$: Calculated: %C 60.00; %H 6.18; %Cl 16.10; %N 3.18. Found: %C 59.6; %H 6.4; %Cl 15.9; %N 3.4.

EXAMPLE 31

6-chloro-4-ethyl-4-phenyl-[4H]-1,3-benzodioxin-2-carboxylic acid (mixture of two racemates diastereoisomers)

4.8 g of sodium were added in small amounts to a stirred mixture of 250 ml of condensed liquid ammonia and 100 mg of ferric nitrate and then a solution of 26.2 g of 5-chloro-α-ethyl-2-hydroxy-α-phenyl-benzene-methanol [prepared by Step A of Example 23 using ethyl bromide] with a melting point of 85° C. in 200 ml of anhydrous toluene was added thereto at 28°–30° C. over 90 minutes. The temperature was raised to disengage the ammonia and the mixture was then refluxed for 3 hours. 100 ml of toluene was added thereto followed by addition of 18 g of potassium dichloroacetate at 50° C. The mixture was refluxed overnight and 9 g of potassium dichloroacetate were added thereto. The mixture was refluxed for 2 more hours and was cooled and poured into water. The organic phase was decanted and the aqueous phase was acidified and extracted with ether. The ether extracts were washed 3 times with 500 ml of water and was extracted 3 times with 300 ml of sodium bicarbonate solution. The combined aqueous phases were washed twice with 500 ml of ether, were acidified with concentrated hydrochloric acid and extracted 3 times with 500 ml of ether. The ether extracts were washed with water, dried over magnesium sulfate and evaporated to dryness under reduced pressure to obtain 27 g of raw 6-chloro-4-ethyl-4-phenyl-[4H]-1,3-benzodioxin-2-carboxylic acid. (mixture of two racemates diastereoisomers).

EXAMPLE 32

A and B isomers of methyl 6-chloro-4-ethyl-4-phenyl-[4H]-1,3-benzodioxin-2-carboxylate Using the procedure of Example 20, 26 g of the product of Example 31 were reacted to obtain 4.5 g of the A isomer of methyl 6-chloro-4-ethyl-4-phenyl-[4H]-1,3-benzodioxin-2-carboxylate and 4 g of the B isomer of the said ester. Crystallization of the A isomer from refluxing methanol yielded 3.5 g of product melting at 128° C. and the B isomer melted at 108° C.

A isomer Analysis: $C_{18}H_{17}ClO_4$: Calculated: %C 64.96; %H 5.15; %Cl 10.65. Found: %C 65.0; %H 5.2; %Cl 10.4.

RMN Spectrum (deuterochloroform-60 MHz):
4-ethyl at 44-51-58 Hz; $CH_3$ at 110 to 160 Hz; $COOCH_3$ at 232 Hz; 2-hydrogen at 314 Hz; aromatic of 1,3-dibenzodioxin at 415 to 450 Hz; 4-phenyl at 445 Hz.

EXAMPLE 33

6-chloro-4-methyl-4-(4-chlorophenyl)-[4H]-1,3-benzodioxin-2-carboxylic acid (mixture of two racemates diastereoisomers)

STEP A: 5-chloro-2-hydroxy-α-methyl-α-(4-chlorophenyl)-benzene-methanol 330 ml of a freshly prepared and filtered solution of magnesium 1-chloro-4-bromo-benzene titrating 0.46 mol/l were added dropwise at 10° to 20° under argon to a magnetically stirred mixture of 130 ml of anhydrous ether and 13.5 g of 2-hydroxy-5-chloroacetophenone in an ice water bath and the mixture was stirred overnight at room temperature. The yellow suspension was iced and 125 ml of iced 2 N aqueous hydrochloric acid were added dropwise thereto. The organic phase was decanted and washed with water, dried over sodium sulfate, treated with activated carbon and vacuum filtered. The filtrate was evaporated to dryness under reduced pressure and the residue was dissolved in 100 ml of cyclohexane. Crystallization occured with stirring and the mixture was vacuum filtered. The precipitate was empasted with a little cyclohexane and dried in an oven to obtain 19.3 g of 5-chloro-2-hydroxy-α-methyl-α-(4-chlorophenyl)-benzene-methanol melting 130° C.

Analysis: $C_{14}H_{12}Cl_2O_2$: Calculated: %C 59.38; %H 4.27; %Cl 25.04. Found: %C 59.7; %H 4.3; %Cl 24.7.

STEP B: 6-chloro-4-methyl-4-(4-chlorophenyl)-[4H]-1,3-benzodioxin-2-carboxylic acid (mixture of two racemates diastereoisomers)

A solution of 16 g of dichloroacetic acid in 100 ml of dioxane was added over 45 minutes to a stirred mixture of 250 ml of dioxane, 25 g of sodium hydride and 1.6 g of dibenzo-18-couronne-6 and a solution of 36.5 g of the product of Step A in 150 ml of dioxane was added thereto at 30° C. over one hour. The mixture was heated at 80° C. for 5 hours, cooled and poured into a water-ice mixture. The mixture was extracted 3 times with 500 ml of ether, was acidified with concentrated hydrochloric acid and was extracted 3 times with 500 ml of ether. The latter ether extracts were extracted with aqueous sodium bicarbonate solution and the aqueous extract was acidified and extracted 4 times with 300 ml of ether. The ether extracts were washed with water, dried over magnesium sulfate and evaporated to dryness under reduced pressure to obtain 40 g of raw 6-chloro-4-ethyl-4-(4-chlorophenyl)-[4H]-1,3-benzodioxin-2-carboxylic acid (mixture of two racemates diastereoisomers).

RMN Spectrum (deuterochloroform-60 MHz):
2-hydrogen at 309 Hz and $CH_3$ at 116 Hz (A isomer); 2-hydrogen at 340 Hz and $CH_3$ at 124 Hz (B isomer); aromatics at 405 to 445 Hz; OH at 510 Hz.

EXAMPLE 34

A isomer of methyl 6-chloro-4-methyl-4-(4-chlorophenyl)-[4H]-1,3-benzodioxin-2-carboxylate A mixture of 40 g of the product of Example 33, 400 ml of methanol and 180 g of a strong sulfonic acid resin was refluxed with stirring for 18 hours, then cooled and vacuum filtered. The filtrate was washed 4 times with 300 ml of ether and was evaporated to dryness under reduced pressure. The residue was taken up in 500 ml of ether and the ether solution was washed 3 times with 300 ml of aqueous sodium bicarbonate solution and 4 times with 500 ml of water. The ether phase was dried over magnesium sulfate and evaporated to dryness under reduced pressure. The residue of 35.5 g was taken up in 100 ml of methanol and the solution stood overnight at room temperature and was vacuum filtered. The product was washed with iced methanol to obtain 10 g of product which was crystallized from methanol standing overnight at room temperature to obtain 9.1 g of the A isomer of methyl 6-chloro-4-ethyl-4-chlorophenyl-[4H]-1,3-benzodioxin-2-carboxylate melting at 108° C.

Analysis: $C_{17}H_{14}Cl_2O_4$: Calculated: %C 57.81; %H 4.0; %Cl 20.0. Found: %C 58.0; %H 4.0; %Cl 19.9.

RMN Spectrum (deuterochloroform-60 MHz):
$CH_3$ at 115 Hz; $COOCH_3$ at 231 Hz; 2-hydrogen at 308 Hz; aromatics at 412 to 442 Hz.

EXAMPLE 35

6-chloro-4-methyl-4-phenyl-[4H]1,3-benzodioxin-2-carboxylic acid (mixture of two racemates diastereoisomers).

A solution of 9.95 g of 5-chloro-2-hydroxy-α-methyl-α-phenyl-benzene-methanol in 150 ml of anhydrous toluene was added dropwise at room temperature to a mixture of 4 g of sodium amide and 50 ml of anhydrous toluene and the mixture was refluxed for 6 hours and cooled to room temperature. 10.25 g of potassium dibromoacetate were added thereto and the mixture was refluxed for another 6 hours and cooled. 200 ml of water were added thereto and the organic phase was decanted and extracted twice with 80 ml of water. The aqueous phase was washed twice with 80 ml of ether and was acidified with 40 ml of 2 N hydrochloric acid. The resulting precipitate was extracted 3 times with 100 ml of ether and the ether extracts were washed twice with 80 ml of water and extracted with 50% of an aqueous 5% sodium bicarbonate solution. The aqueous phase was washed 3 times with 80 ml of ether and acidified with 90 ml of 2 N hydrochloric acid solution. The mixture was extracted 4 times with 100 ml of ether and the combined ether extracts were washed with water, dried over magnesium sulfate, treated with activated carbon and evaporated to dryness under reduced pressure to obtain 7.85 g of raw product. The latter was taken up in hexane and vacuum filtered and the recovered crystals were dried to obtain 6 g of 6-chloro-4- methyl-4-phenyl-[4H]-1,3-benzodioxin-2-carboxylic acid (mixture of two racemates diastereoisomers) melting at 144° C.

RMN Spectrum (deuterochloroform-60 MHz):

$CH_3$ at 117 Hz; and 2-hydrogen at 312 Hz (A isomer); 2-hydrogen at 342.5 Hz and $CH_3$ at 125.5 Hz (B isomer); aromatics at 405 to 450 Hz; OH at ≃350 Hz.

EXAMPLE 36

6-chloro-4-methyl-4-phenyl-[4H]-1,3-benzodioxin-2-carboxylic acid (mixture of two racemates diastereoisomers)

60 mg of dibenzo-18-couronne-6 were added at 150° C. to a mixture of 10 ml of dioxane and 1.35 g of sodium hydride as a 50% oil suspension and then a solution of 0.61 ml of dichloroacetic acid in 10 ml of dioxane was added thereto over 5 minutes followed by addition of solution of 1.25 g of 2-hydroxy-5-chloro-α-methylbenzhydrol in 5 ml of dioxane over 10 minutes at 20° C. The mixture was heated for 6 hours at 80° C., cooled to 20° C. and 2 ml of methanol were added thereto. The mixture was poured into iced water and was extracted three times with ethyl acetate. The organic extracts were washed 5 times with 0.1 N sodium hydroxide and the combined aqueous phases were acidified to a pH of 1 with 2 N hydrochloric acid and extracted 3 times with methylene chloride. The organic extracts were dried and evaporated to dryness to obtain raw 6-chloro-4-methyl-4-phenyl-[4H]-1,3-benzodioxin-2-carboxylic acid (mixture of two racemates diastereoisomers).

EXAMPLE 37 piperidine salt of A isomer of 6-chloro-4-methyl-4-phenyl-[4H]-1,3-benzodioxin-2-carboxylic acid 0.8 ml of piperidine was added at 10° C. to a solution of the product of Example 36 in 4 ml of ethyl acetate and crystallization was started by scratching. After 15 minutes, the mixture was vacuum filtered and the product was washed with ethyl acetate and ether and dried at 20° C. to obtain 855 mg of product.

The mother liquor of the crystallization were diluted with methylene chloride and the mixture was washed with iced hydrochloric acid, dried and evaporated to dryness. The residue was taken up in 12 ml of methylene chloride and 0.6 ml of ether-boron trifluoride complex was added thereto. The mixture stood at 20° C. for 30 minutes and was poured into ice. The mixture was washed twice with water and the aqueous phase was extracted with methylene chloride. The organic phase was dried and evaporated to dryness and the residue was taken up in 2 ml of ethyl acetate and 0.4 ml of piperidine. Crystallization resulted in 545 mg of product. Another operation was effected in the same manner with the mother liquors to obtain 130 mg of product for a total yield of 1.53 g of the piperidine salt of the A isomer of 6-chloro-4-methyl-4-phenyl-[4H]-1,3-benzodioxin-2-carboxylic acid melting at ≃165° C.

EXAMPLE 38

A isomer of 6-chloro-4-methyl-4-phenyl-[4H]-1,3-benzodioxin-2-carboxylic acid

The 1.53 g of the product of Example 37 was dissolved in a mixture of methylene chloride and N hydrochloric acid and the solution was washed with water, dried, treated with activated carbon and concentrated while adding cyclohexane to a volume of 3 ml. The mixture was vacuum filtered and the product was washed with cyclohexane and dried at 40° C. under reduced pressure to obtain 1.1 g of the A isomer of 6-chloro-4-phenyl-[4-H]-1,3-benzodioxin-2-carboxylic acid melting at 175° C. and identical to the A isomer of Example 3.

EXAMPLE 39

STEP A: 4-chloro-2-hydroxy-α-methyl-α-phenyl-benzene-methanol

A mixture of 16.2 g of 2-hydroxy-4-(chlorophenyl)ethanone in 170 ml of ether was stirred and added dropwise at room temperature to 315 ml of a solution of phenyl magnesium-bromide in ether (0.8 M/liter). The mixture was stirred overnight at room temperature, was poured into ice, and the mixture was acidified with 40 ml of hydrochloric acid and extracted 4 times with 250 ml of ether. The decanted organic phases were washed 4 times with 150 ml of water and dried over magnesium sulfate with activated carbon. The obtained product was added to 50 ml of cyclohexane and dried under reduced pressure over 24 hours to obtain 14.45 g of 4-chloro-2-hydroxy-α-methyl-α-phenyl benzene methanol. A sample of 0.200 g crystallized from cyclohexane melted at 82° C.

Analysis: $C_{14}H_{13}ClO_2$: Calculated: %C 67.61; %H 5.27; %Cl 14.25. Found: %C 67.3; %H 5.1; %Cl 14.3.

STEP B: 7-chloro-4-methyl-4-phenyl-[4H]-1,3-benzodioxin-2-carboxylic acid (mixture of two racemates diastereoisomers)

A mixture of 9.85 g of sodium hydride as a 50% oil suspension, 100 ml of dioxane, 0.73 g of dibenzo-18-couronne-6 was stirred and a solution of 11.31 g of dichloroacetic acid in 120 ml of dioxane was added thereto at room temperature with stirring. Then, a solution of 14.550 g of 4-chloro-2-hydroxy-α-methyl-α-phenyl benzene methanol in 200 ml dioxane was added thereto dropwise and the mixture was then refluxed for 6 hours at 95° C. and then returned to room temperature. The reaction mixture was poured into ice and 10 ml of 2 N sodium hydroxide were added thereto. The aqueous phase was washed with 300 ml of ether, was acidified with 20 ml of concentrated hydrochloric acid and then was extracted 3 times with 250 ml of ether. The ether extracts were washed twice with 100 ml of water and the acid of the organic phase was extracted twice with 250 ml of a 5% aqueous solution of sodium bicarbonate. The aqueous phase was washed with 100 ml of ether and was acidified again with 50 ml of concentrated hydrochloric acid. The acid was again extracted 4 times with 250 ml of ether, and the decanted organic phase was washed 3 times with 100 ml of water, dried over magnesium sulfate, treated with activated carbon, filtered and evaporated to dryness under reduced pressure to obtain 19.5 g of 7-chloro-4-methyl-4-phenyl-[4H]-1,3-benzodioxin-2-carboxylic acid (mixture of two racemates of diastereoisomers).

RMN Spectrum (deuterochloroform-60 MHz):

2-hydrogen at 312 Hz; hydrogens of 4-$CH_3$ at 116 Hz; (corresponding to A isomer).

2-hydrogen at 343 Hz; hydrogens of 4-$CH_3$ at 125 Hz; (corresponding to B isomer).

EXAMPLE 40

A isomer of methyl 7-chloro-4-methyl-4-phenyl-[4H]-1,3-benzodioxin-2-carboxylate 19.5 g of the product of Example 39 dissolved in 300 ml of methylene chloride were added dropwise at 15° C. to 9.1 g of boron trifluoride etherate. The mixture was stirred for two hours at room temperature, and then 300 ml of methanol were added thereto and the mixture was stirred for 24 hours and poured into 500 ml of a saturated sodium chloride solution. The mixture was extracted 3 times with 200 ml of methylene chloride and the resulting organic phase was washed with 50 ml of a saturated aqueous solution of sodium bicarbonate. The decanted organic phase was washed twice with 50 ml of water (until neutral), dried over magnesium sulfate, treated with activated carbon, filtered and evaporated to dryness under reduced pressure to obtain 17.1 g of residue. 16.6 g of the residue were crystallized from methanol to obtain 10.35 g of A isomer of methyl 7-chloro-4-methyl-4-phenyl-[4H]-1,3-benzodioxin-2-carboxylate melting at 144° C.

Analysis: $C_{17}H_{15}ClO_4$: Calculated: %C 64.05; %H 4.74; %Cl 11.12. Found: %C 63.8; %H 4.7; %Cl 11.1.

RMN Spectrum (deuterochloroform-60 MHz):
2-hydrogen at 310 Hz; hydrogens of 4-$CH_3$ at 115 Hz; hydrogens of $COOCH_3$ at 230 Hz.

EXAMPLE 41

Hydrochloride of A isomer of 2-(dimethylamino)-ethyl 6-chloro-4-methyl-4-phenyl-[4H]-1,3-benzodioxin-2-carboxylate A mixture of 7.1 g of A isomer of methyl 6-chloro-4-methyl-4-phenyl-[4H]-1,3-benzodioxin-2-carboxylate (obtained as in Example 2), 2.5 g of dimethylaminoethanol, 100 ml of anhydrous toluene and traces of sodium hydride was refluxed with stirring for 5 hours, cooled, treated with activated carbon and filtered. The filtrate was added to 7 ml of a 5 N ether solution of hydrochloric acid and was filtered. The obtained precipitate was crystallized from 40 ml of isopropanol to obtain 4.8 g of hydrochloride of A isomer of 2-(dimethylamino)-ethyl 6-chloro-4-methyl-4-phenyl-[4H]-1,3-benzodioxin-2-carboxylate melting at 185° C.

Analysis: $C_{20}H_{22}ClNO_4$: Calculated: %C 58.26; %H 5.62; %Cl 17.20; %N 3.40. Found: %C 58.1; %H 5.9; %Cl 17.0; %N 3.5.

RMN Spectrum (deuterochloroform-60 MHz):
2-hydrogen at 312 Hz; hydrogens of COO—$CH_2$—$CH_2$ at 285 and 235 Hz;

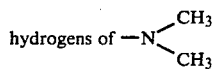

at 172 Hz; hydrogens of 4-$CH_3$ at 115 Hz; and aromatic hydrogens at 411 and 441 Hz.

EXAMPLE 42

Tablets were prepared containing 300 mg of the A isomer of 6-chloro-4-methyl-4-phenyl-[4H]-1,3-benzodioxin-2-carboxylic acid or the A isomer of Example 21 and sufficient excipient of lactose, starch, talc and magnesium stearate to obtain a tablet weighing 500 mg.

Tablets were prepared containing 300 mg of the A isomer of 6-chloro-4-methyl-4-phenyl-[4H]-1,3-benzodioxin-2-carboxylic acid and sufficient excipient of talc, magnesium stearate, aerosil to obtain a tablet weighing 500 mg.

Gelules were prepared from 25 mg of the A isomer of methyl 6-chloro-4-methyl-4-phenyl-[4H]-1,3-benzodioxin-2-carboxylate acid or 250 mg of the d-isomer of Example 18 and sufficient excipient of talc, aerosil and magnesium stearate to obtain a gelule weighing 500 mg.

EXAMPLE 43

Tablets were prepared containing 300 mg of the A isomer of methyl 7-chloro-4-methyl-4-phenyl-[4H]-1,3-benzodioxin-2-carboxylate (compound of Example 40) and sufficient excipient of talc, magnesium stearate and aerosil for a final weight of 500 mg.

Gelules were prepared containing 250 mg of the hydrochloride of A isomer of 2-(dimethylamino)-ethyl 6-chloro-4-methyl-4-phenyl-[4H]-1,3-benzodioxin-2-carboxylate (compound of Example 41) and sufficient excipient of talc, magnesium stearate and aerosil for a final weight of 500 mg.

PHARMACOLOGICAL DATA

A. Hypolipemiant Activity

This test was effected on groups of 8 male rats of the Sprague Dawley S.P.F. strain weighing about 200 g and the animals received a regime containing 50% of saccharose and which was rich in cholesterol (1%). The rats were treated over 10 days with the test products which were administered through an esophague tube as a suspension in water containing carboxymethylcellulose. The animals were killed 16 hours after the last administration of the test product by an abdominal puncture and from the blood sample with sodium heparinate, the levels of triglycerides, cholesterol and total lipids were determined by the following methods.

The triglyceride level was determined by the semi-automatic technique of Kessler et al [Automation in Analytical Chemistry, 1965, p. 341] modified by Claude et al [Ann. Biol. Clin., Vol. 26 3-4 (1968), p. 451]. The cholesterol levels were determined by the technique of Levine [Symposium Technicon, Vol. I. (1967), p. 25] adapted to auto-analyzer system I. The nephelometric level of total lipids was determined semi-automatically by the method of Girard et al [Symposium Technicon, 1970]. The variations expressed in percentages of the level of triglycerides, cholesterol and total lipids after administration of the various dosage of the test products in the treated animals as compared to the untreated controls and the results are reported in Table I.

TABLE I

| Products of Example | Doses in mg/kg day | % Variation of levels | | |
|---|---|---|---|---|
| | | Triglycerides | Cholesterol | Total Lipids |
| 1 | 5 | −11 | −22 | −26 |
| 3 | 2 | −12 | −36 | −38 |
| 16 Isomer A | 2 | −32 | −17 | −25 |
| 17 Isomer A | 2 | −57 | −43 | −47 |
| 18 Isomer A 1 form | 2 | −53 | −47 | −53 |
| 20 Isomer A | 1 | −13 | −36 | −32 |
| 21 Isomer A | 1 | −62 | −11 | −25 |
| 41 Isomer A | 5 | −43 | −40 | −49 |

B. Acute Toxicity

The acute toxicity was determined on groups of 5 mice weighing about 18 to 22 g and the test products were intraperitoneally administered in suspension in an aqueous carboxymethylcellulose. The mice were observed for one week and $DL_{50}$ dose was determined as reported in Table II.

TABLE II

| Product of Example | $DL_{50}$ in mg/kg |
|---|---|
| 1 | 130 |
| 3 | 150 |
| 16 Isomer A | ≃800 |
| 17 Isomer A | ≃200 |
| 18 Isomer A 1 form | ≃250 |
| 20 Isomer A | ≦1000 |
| 21 Isomer A | ≃150 |
| 41 Isomer A | ≃200 |

Various modifications of the products and process of the invention may be made without departing from the spirit or scope thereof and it should be understood that the invention is intended to be limited only as defined in the appended claims.

We claim:

1. A compound selected from the group consisting of racemic mixtures or optically active isomers of 1,3-benzodioxins of the formula

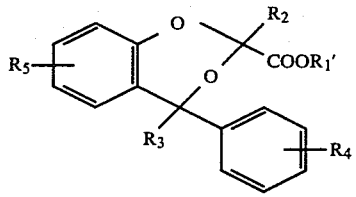

wherein $R_1'$ is selected from the group consisting of hydrogen, alkali metal, alkaline earth metal, —$NH_4$, aluminum, non-toxic, pharmaceutically acceptable amines, alkyl of 1 to 5 carbon atoms, 2,3-dihydroxypropanyl, (2,2-dimethyl-1,3-dioxolan-4-yl)-methyl and dialkylaminolakyl with alkyls of 1 to 4 carbon atoms, $R_2$ is selected from the group consisting of hydrogen and alkyl of 1 to 5 carbon atoms, $R_3$ is selected from the group consisting of hydrogen, alkyl of 1 to 5 carbon atoms and phenyl and $R_4$ and $R_5$ are individually selected from the group consisting of hydrogen and halogen and the non-toxic, pharmaceutically acceptable acid addition salts where $R_1'$ is dialkylaminoalkyl with the proviso that $R_2$ and $R_3$ are not simultaneously hydrogen.

2. A compound of claim 1 wherein $R_1'$ is selected from the group consisting of hydrogen, alkyl of 1 to 5 carbon atoms, alkali metal, alkaline earth metal, aluminum, —$NH_4$ and amines.

3. A compound of claim 1 wherein $R_1'$ is selected from the group consisting of hydrogen, methyl, alkali metal, alkaline earth metal, aluminum, —$NH_4$ and an amine, $R_2$ is selected from the group consisting of hydrogen and methyl, $R_3$ is selected from the group consisting of hydrogen, methyl and phenyl, $R_4$ is hydrogen and $R_5$ is selected from the group consisting of hydrogen and chlorine.

4. A compound of claim 3 wherein $R_2$ is hydrogen and $R_5$ is chlorine.

5. A compound of claim 1 selected from the group consisting of methyl 6-chloro-4-methyl-4-phenyl-[4H]-1,3-benzodioxin-2-carboxylate, methyl 6-chloro-4-methyl-4-(3-chlorophenyl)-[4H]-1,3-benzodioxin-2-carboxylate, ethyl 6-chloro-4-methyl-4-phenyl-[4H]-1,3-benzodioxin-2-carboxylate, 6-chloro-4-methyl-4-phenyl-[4H]-1,3-benzodioxin-2-carboxylic acid and its sodium salt, 6-chloro-2,4-dimethyl-4-phenyl-[4H]-1,3-benzodioxin-2-carboxylic acid, 6-chloro-4-methyl-4-(3-chloro-phenyl)-[4H]-1,3-benzodioxin-2-carboxylic acid, piperidine salt of 2 racemates A and B diastereoisomers of 6-chloro-4-methyl-4-phenyl-[4H]-1,3-benzodioxin-2-carboxylic acid, d and 1 isomers of two racemate A and B diastereoisomers of 6-chloro-4-methyl-4-phenyl-[4H]-1,3-benzodioxin-2-carboxylic acid and racemic and optically active forms of (2,2-dimethyl-1,3-dioxolan-4-yl)-methyl 6-chloro-4-methyl-4-phenyl-[4H]-1,3-benzodioxin-2-carboxylate, 2,3-dihydroxypropanyl 6-chloro-4-methyl-4-phenyl-[4H]-1,3-benzodioxin-2-carboxylate and 2-(diethylamino)-ethyl 6-chloro-4-methyl-4-phenyl-[4H]-1,3-benzodioxin-2-carboxylate and the non-toxic, pharmaceutically acceptable acid addition salts of the latter, 6-chloro-4,4-diphenyl-[4H]-1,3-dibenzodioxin-2-carboxylic acid and its methyl ester, 4-methyl-4-phenyl-1,3-benzodioxin-2-carboxylic acid, methyl 6-chloro-4-isopropyl-4-phenyl-[4H]-1,3-benzodioxin-2-carboxylate, methyl 6-chloro-4-tert.-butyl-4-phenyl-[4H]-1,3-benzodioxin-2-carboxylate, methyl 6-fluoro-4-methyl-4-phenyl-[4H]-1,3-benzodioxin-2-carboxylate, methyl 6-chloro-4-ethyl-4-phenyl-[4H]-1,3-benzodioxin-2-carboxylate, methyl 6-chloro-4-methyl-4-(4-chlorophenyl)-[4H]-1,3-benzodioxin-2-carboxylate and methyl 7-chloro-4-methyl-4-phenyl-[4H]-1,3-benzodioxin-2-carboxylate.

6. A compound of claim 1 which is selected from the group consisting of the A isomer of methyl 6-chloro-4-methyl-4-phenyl-[4H]-1,3-benzodioxin-2-carboxylate, the A isomer of methyl 6-chloro-4-methyl-4-(3-chlorophenyl)-[4]-1,3-benzodioxin-2-carboxylate and the A isomer of ethyl 6-chloro-4-methyl-4-phenyl-[4H]-1,3-benzodioxin-2-carboxylate.

7. A compound of claim 1 selected from the group consisting of the A isomer of 6-chloro-4-methyl-4-phenyl-[4H]-1,3-benzodioxin-2-carboxylic acid and its sodium salt, the A isomer of 6-chloro-2,4-dimethyl-4-phenyl-[4H]-1,3-benzodioxin-2-carboxylic acid, the A isomer of 6-chloro-4-methyl-4-(3-chlorophenyl)-[4H]-1,3-benzodioxin-2-carboxylic acid and the d and 1 isomers of the A isomer of 6-chloro-4-methyl-4-phenyl-[4H]-1,3-benzodioxin-2-carboxylic acid.

8. The A isomer of the 7-chloro-4-methyl-4-phenyl[4H]-1,3-benzodioxin-2-carboxylic acid having a RMN Spectrum (deuterochloroform, basic frequency 60 MHz): 2-hydrogen at 312 Hz and 4-$CH_3$ at 116 Hz.

9. A compound of claim 1 selected from the group consisting of 2-(dimethylamino)-ethyl 6-chloro-4-methyl-4-phenyl-[4H]-1,3-benzodioxin-2-carboxylate mixtures or optically active isomers and acid addition salts thereof.

10. The hydrochloride of A isomer of 2-(dimethylamino)ethyl 6-chloro-4-methyl-4-phenyl-[4H]-1,3-benzodioxin-2-carboxylate having a RMN Spectrum (deuterochloroform, basic frequency 60 MHz): 2-hydrogen at 312 Hz and 4-$CH_3$ at 115 Hz.

11. An hypolipemiant composition comprising an nypolipemiantly effective amount of at least one compound selected from the group consisting of racemic mixtures or optically active isomers of 1,3-benzodioxins of the formula

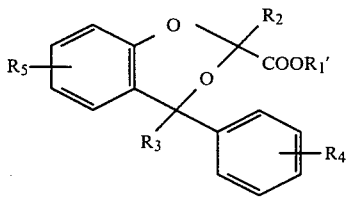

wherein R₁' is selected from the group consisting of hydrogen, alkali metal, alkaline earth metal, —NH₄, aluminum, non-toxic, pharmaceutically acceptable amines, alkyl of 1 to 5 carbon atoms, 2,3-dihydroxypropanyl, (2,2-dimethyl-1,3-dioxolan-4-yl)-methyl and dialkylaminoalkyl with alkyls of 1 to 4 carbon atoms, R₂ is selected from the group consisting of hydrogen and alkyl of 1 to 5 carbon atoms, R₃ is selected from the group consisting of hydrogen, alkyl of 1 to 5 carbon atoms and phenyl and R₄ and R₅ are individually selected from the group consisting of hydrogen and halogen and the non-toxic, pharmaceutically acceptable acid addition salts when R₁' is dialkylaminoalkyl and an inert pharmaceutical carrier.

12. A composition of claim 11 wherein R₁' is selected from the group consisting of hydrogen, alkyl of 1 to 5 carbon atoms, alkali metal, alkaline earth metal, aluminum, —NH₄ and amines.

13. A composition of claim 11 wherein R₁' is selected from the group consisting of hydrogen, methyl, alkali metal, alkaline earth metal, aluminum, —NH₄ and an amine, R₂ is selected from the group consisting of hydrogen and methyl, R₃ is selected from the group consisting of hydrogen, methyl and phenyl, R₄ is hydrogen and R₅ is selected from the group consisting of hydrogen and chlorine.

14. A composition of claim 13 wherein R₂ is hydrogen and R₅ is chlorine.

15. A composition of claim 11 selected from the group consisting of methyl 6-chloro-4-methyl-4-phenyl-[4H]-1,3-benzodioxin-2-carboxylate, methyl 6-chloro-4-methyl-4-(3-chlorophenyl)-[4H]-1,3-benzodioxin-2-carboxylate, ethyl 6-chloro-4-methyl-4-phenyl-[4H]-1,3-benzodioxin-2-carboxylate, 6-chloro-4-methyl-4-phenyl-[4H]-1,3-benzodioxin-2-carboxylic acid and its sodium salt, 6-chloro-2,4-dimethyl-4-phenyl-[4H]-1,3-benzodioxin-2-carboxylic acid, 6-chloro-4-methyl-4-(3-chlorophenyl)-[4H]-1,3-benzodioxin-2-carboxylic acid, piperidine salts of 2 racemates A and B diastereoisomers of 6-chloro-4-methyl-4-phenyl-[4H]-1,3-benzodioxin-2-carboxylic acid, d and l isomers of two racemate A and B diastereoisomers of 6-chloro-4-methyl-4-phenyl-[4H]-1,3-benzodioxin-2-carboxylic acid and racemic and optically active forms of (2,2-dimethyl-1,3-dioxolan-4-yl) methyl 6-chloro-4-methyl-4-phenyl-[4H]-1,3-benzodioxin-2-carboxylate, 2,3-dihydroxypropanyl 6-chloro-4-methyl-4-phenyl-[4H]-1,3-benzodioxin-2-carboxylate and 2-(diethylamino) ethyl 6-chloro-4-methyl-4-phenyl-[4H]-1,3-benzodioxin-2-carboxylate and the non-toxic, pharmaceutically acceptable acid addition salts of the latter, 6-chloro-4,4-diphenyl-[4H]-1,3-benzodioxin-2-carboxylic acid and its methyl ester, 4-methyl-4-phenyl-1,3-benzodioxin-2-carboxylic acid, methyl 6-chloro-4-isopropyl-4-phenyl-[4H]-1,3-benzodioxin-2-carboxylate, methyl 6-chloro-4-tert.-butyl-4-phenyl-[4H]-1,3-benzodioxin-2-carboxylate, methyl 6-fluoro-4-methyl-4-phenyl-[4H]-1,3-benzodioxin-2-carboxylate, methyl 6-chloro-4-ethyl-4-phenyl-[4H]-1,3-benzodioxin-2-carboxylate methyl 6-chloro-4-methyl-4-(4-chlorophenyl)-[4H]-1,3-benzodioxin-2-carboxylate methyl 7-chloro-4-methyl-4-phenyl-[4H]-1,e-benzodioxin-2-carboxylate, and 2-(dimethylamino) ethyle 6-chloro-4-methyl-4-phenyl-[4H]-1,3-benzodioxin-2-carboxylate and the non-toxic, pharmaceutically acceptable acid addition salts of the latter.

16. A composition of claim 11 selected from the group consisting of the A isomer of methyl 6-chloro-4-methyl-4-phenyl-[4H]-1,3-benzodioxin-2-carboxylate, the A isomer of methyl 6-chloro-4-methyl-4-(3-chlorophenyl)-[4H]-1,3-benzodioxin-2-carboxylate and the A isomer of ethyl 6-chloro-4-methyl-4-phenyl-[4H]-1,3-benzodioxin-2-carboxylate.

17. A composition of claim 11 selected from the group consisting of the A isomer of 6-chloro-4-methyl-4-phenyl-[4H]-1,3-benzodioxin-2-carboxylic acid and its sodium salt, the A isomer of 6-chloro-2,4-dimethyl-4-phenyl-[4H]-1,3-benzodioxin-2-carboxylic acid, the A isomer of 6-chloro-4-methyl-4-(3-chlorophenyl)-[4H]-1,3-benzodioxin-2-carboxylic acid and the d and l isomers of the A isomer of 6-chloro-4-methyl-4-phenyl-[4H]-1,3-benzodioxin-2-carboxylic acid.

18. A composition of claim 11 comprising the A isomer of the 7-chloro-4-methyl-4-phenyl-[4H]-1,3-benzodioxin-2-carboxylic acid having a RMN Spectrum (deuterochloroform, basic frequency 60 MHz) 2-hydrogen at 312 Hz and 4-CH₃ at 116 Hz.

19. A composition of claim 11 selected from the group consisting of 2-(dimethylamino)-ethyl 6-chloro-4-methyl-4-phenyl-[4H]-1,3-benzodioxin-2-carboxylate, mixtures or optically active isomers and acid addition salts thereof.

20. A composition of claim 11 comprising the hydrochloride of A isomer of 2-(dimethylamino)-ethyl 6-chloro-4-methyl-4-phenyl-[4H]-1,3-benzodioxin-2-carboxylate having a RMN Spectrum (deuterochloroform, basic frequency 60 MHz), 2-hydrogen at 312 Hz and 4-CH₃ at 115 Hz.

21. A method of inducing hypolipemiant activity in warm-blooded animals comprising administering a warm-blooded animals an hypolipemiantly effective amount of at least one compound selected from the group consisting of racemic mixtures or optically active isomers of 1,3-benzodioxins of the formula

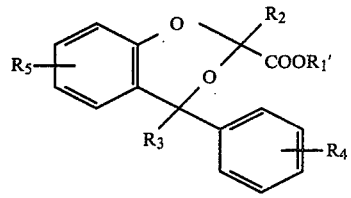

wherein R₁' is selected from the group consisting of hydrogen, alkali metal, alkaline earth metal, —NH₄, aluminum, non-toxic, pharmaceutically acceptable amines, alkyl of 1 to 5 carbon atoms, 2,3-dihydroxypropanyl, (2,2-dimethyl-1,3-dioxolan-4-yl)-methyl and dialkylaminoalkyl with alkyls of 1 to 4 carbon atoms, R₂ is selected from the group consisting of hydrogen and alkyl of 1 to 5 carbon atoms, R₃ is selected from the group consisting of hydrogen, alkyl of 1 to 5 carbon atoms and phenyl and R₄ and R₅ are individually selected from the group consisting of hydrogen and halogen and the non-toxic, pharmaceutically acceptable acid addition salts where R₁' is dialkylaminoalkyl.

22. A method of claim 21 wherein R₁' is selected from the group consisting of hydrogen, alkyl of 1 to 5 carbon atoms, alkali metal, alkaline earth metal, aluminum, —NH₄ and amines.

23. A method of claim 21 wherein R₁' is selected from the group consisting of hydrogen, methyl, alkali metal, alkaline earth metal, aluminum, —NH₄ and an amine, R₂ is selected from the group consisting of hydrogen and methyl, R₃ is selected from the group consisting of hydrogen, methyl and phenyl, R₄ is hydrogen and R₅ is selected from the group consisting of hydrogen and chlorine.

24. A method of claim 23 wherein R₂ is hydrogen and R₅ is chlorine.

25. A method of claim 21 selected from the group consisting of methyl 6-chloro-4-methyl-4-phenyl-[4H]-1,3-benzodioxin-2-carboxylate, methyl 6-chloro-4-methyl-4-(3-chlorophenyl)-[4H]-1,3-benzodioxin-2-carboxylate, ethyl 6-chloro-4-methyl-4-phenyl-[4H]-1,3-benzodioxin-2-carboxylate, 6-chloro-4-methyl-4-phenyl-[4H]-1,3-benzodioxin-2-carboxylic acid and its sodium salt, 6-chloro-2,4-dimethyl-4-phenyl-[4H]-1,3-benzodioxin-2-carboxylic acid, 6-chloro-4-methyl-4-(3-chlorophenyl)-[4H]-1,3-benzodioxin-2-carboxylic acid, piperidine salts of 2 racemates A and B diastereoisomers of 6-chloro-4-methyl-4-phenyl-[4H]-1,3-benzodioxin-2-carboxylic acid, d and l isomers of two racemate A and B diastereoisomers of 6-chloro-4-methyl-4-phenyl-[4H]-1,3-benzodioxin-2-carboxylic acid and racemic and optically active forms of (2,2-dimethyl-1,3-dioxolan-4-yl)-methyl 6-chloro-4-methyl-4-phenyl-[4H]-1,3-benzodioxin-2-carboxylate, 2,3-dihydroxypropanyl 6-chloro-4-methyl-4-phenyl-[4H]-1,3-benzodioxin-2-carboxylate and 2-(diethylamino)-ethyl 6-chloro-4-methyl-4-phenyl-[4H]-1,3-benzodioxin-2-carboxylate and the non-toxic, pharmaceutically acceptable acid addition salts of the latter, 6-chloro-4,4-diphenyl-[4H]-1,3-benzodioxin-2-carboxylic acid and its methyl ester, 4-methyl-4-phenyl-1,3-benzodioxin-2-carboxylic acid, methyl 6-chloro-4-isopropyl-4-phenyl-[4H]-1,3-benzodioxin-2-carboxylate, methyl 6-chloro-4-tert.-butyl-4-phenyl-[4H]-1,3-benzodioxin-2-carboxylate, methyl 6-fluoro-4-methyl-4-phenyl-[4H]-1,3-benzodioxin-2-carboxylate, methyl 6-chloro-4-ethyl-4-phenyl-[4H]-1,3-benzodioxin-2-carboxylate, methyl 6-chloro-4-methyl-4-(4-chlorophenyl)-[4H]-1,3-benzodioxin-2-carboxylate, methyl 7-chloro-4-methyl-4-phenyl[4H]-1,3-benzodioxin-2-carboxylate and 2-(dimethylamino)ethyl 6-chloro-4-methyl-4-phenyl-[4H]-1,3-benzodioxin-2-carboxylate and the non-toxic pharmaceutically acceptable addition salts of the latter.

26. A method of claim 21 selected from the group consisting of the A isomer of methyl 6-chloro-4-methyl-4-phenyl-[4H]-1,3-benzodioxin-2-carboxylate, the A isomer of methyl 6-chloro-4-methyl-4-(3-chlorophenyl)-[4H]-1,3-benzodioxin-2-carboxylate and the A isomer of ethyl 6-chloro-4-methyl-4-phenyl-[4H]-1,3-benzodioxin-2-carboxylate.

27. A method of claim 21 selected from the group consisting of the A isomer of 6-chloro-4-methyl-4-phenyl-[4H]-1,3-benzodioxin-2-carboxylic acid and its sodium salt, the A isomer of 6-chloro-2,4-dimethyl-4-phenyl-[4H]-1,3-benzodioxin-2-carboxylic acid, the A isomer of 6-chloro-4-methyl-4-(3-chlorophenyl-[4H]-1,3-benzodioxin-2-carboxylic acid and the d and l isomer of the A isomer of 6-chloro-4-methyl-4-phenyl-[4H]-1,3-benzodioxin-2-carboxylic acid.

28. A method of claim 21 comprising the A isomer of 7-chloro-4-methyl-4-phenyl[4H]-1,3-benzodioxin-2-carboxylic acid having a RMN Spectrum (deuterochloroform, basic frequency 60 MHz) 2-hydrogen at 312 Hz and 4-CH₃ at 116 Hz.

29. A method of claim 21 selected from the group consisting of 2-(dimethylamino)-ethyl 6-chloro-4-methyl-4-phenyl-[4H]-1,3-benzodioxin-2-carboxylate, mixtures or optically active isomers and acid addition salts thereof.

30. A method of claim 21 comprising the hydrochloride of A isomer of 2-(dimethylamino)-ethyl 6-chloro-4-methyl-4-phenyl-[4H]-1,3-benzodioxin-2-carboxylate having a RMN Spectrum (deuterochloroform, basic frequency 60 MHz), 2-hydrogen at 312 Hz and 4-CH₃ at 115 Hz.

* * * * *